US010238537B2

United States Patent
Dai et al.

(10) Patent No.: US 10,238,537 B2
(45) Date of Patent: Mar. 26, 2019

(54) SYSTEMS AND METHODS FOR CORRECTING HIGH ORDER ABERRATIONS IN LASER REFRACTIVE SURGERY

(75) Inventors: Guangming Dai, Fremont, CA (US); Junzhong Liang, Fremont, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 2504 days.

(21) Appl. No.: 13/051,452

(22) Filed: Mar. 18, 2011

(65) Prior Publication Data

US 2011/0166558 A1 Jul. 7, 2011

Related U.S. Application Data

(63) Continuation of application No. 10/825,864, filed on Apr. 16, 2004, now Pat. No. 7,926,490.

(60) Provisional application No. 60/463,873, filed on Apr. 18, 2003.

(51) Int. Cl.
*A61B 18/20* (2006.01)
*A61F 9/008* (2006.01)

(52) U.S. Cl.
CPC ......... *A61F 9/008* (2013.01); *A61F 9/00806* (2013.01); *A61F 9/00817* (2013.01); *A61F 2009/0088* (2013.01); *A61F 2009/00844* (2013.01); *A61F 2009/00846* (2013.01); *A61F 2009/00848* (2013.01); *A61F 2009/00857* (2013.01); *A61F 2009/00872* (2013.01); *A61F 2009/00897* (2013.01)

(58) Field of Classification Search
CPC .. A61F 9/008; A61F 9/00806; A61F 9/00825; A61F 9/00827; A61F 9/00829; A61F 2009/00844; A61F 2009/00848; A61F 2009/00861; A61F 2009/00872; A61F 2009/00878; A61F 2009/0088; A61F 2009/00882
USPC ...... 606/3–6, 10–12; 351/205–208, 211, 212
See application file for complete search history.

(56) References Cited

U.S. PATENT DOCUMENTS

| | | | |
|---|---|---|---|
| 4,665,913 A | 5/1987 | L'Esperance, Jr. | |
| 4,669,466 A * | 6/1987 | L'Esperance | A61B 3/107 348/78 |
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 5,108,388 A | 4/1992 | Trokel | |
| 5,163,934 A | 11/1992 | Munnerlyn | |
| 5,207,668 A | 5/1993 | L'Esperance, Jr. | |
| 5,219,343 A | 6/1993 | L'Esperance, Jr. | |
| 5,646,791 A | 7/1997 | Glockler | |

(Continued)

FOREIGN PATENT DOCUMENTS

WO 02/07660 A 1/2002

*Primary Examiner* — Ahmed Farah
(74) *Attorney, Agent, or Firm* — Johnson & Johnson Surgical Vision, Inc.

(57) ABSTRACT

Optical correction methods, devices, and systems reduce optical aberrations or inhibit refractive surgery induced aberrations. Error source control and adjustment or optimization of ablation profiles or other optical data address high order aberrations. A simulation approach identifies and characterizes system factors that can contribute to, or that can be adjusted to inhibit, optical aberrations. Modeling effects of system components facilitates adjustment of the system parameters.

28 Claims, 26 Drawing Sheets

(56) References Cited

U.S. PATENT DOCUMENTS

| | | |
|---|---|---|
| 5,683,379 A | 11/1997 | Hohla |
| 5,713,892 A | 2/1998 | Shimmick |
| 5,807,379 A | 9/1998 | L'Esperance, Jr. |
| 6,004,313 A | 12/1999 | Shimmick et al. |
| 6,095,651 A | 8/2000 | Williams et al. |
| 6,203,539 B1 | 3/2001 | Shimmick et al. |
| 6,245,059 B1 | 6/2001 | Clapham |
| 6,271,915 B1 | 8/2001 | Frey et al. |
| 6,315,413 B1 | 11/2001 | Shimmick et al. |
| 6,331,177 B1 | 12/2001 | Munnerlyn et al. |
| 6,428,533 B1 | 8/2002 | Bille |
| 6,547,393 B2 | 4/2003 | Ruiz |
| 6,673,062 B2 * | 1/2004 | Yee .................. A61F 9/008 351/211 |
| 6,887,232 B2 | 5/2005 | Bille |
| 7,232,436 B2 | 6/2007 | Bille |
| 7,273,277 B2 | 9/2007 | Sarver |
| 7,296,893 B2 | 11/2007 | Dai |
| 7,460,288 B2 | 12/2008 | Liang |
| 7,926,490 B2 | 4/2011 | Dai et al. |
| 2003/0053030 A1 | 3/2003 | Levine |
| 2006/0173445 A1 | 8/2006 | Bille |
| 2008/0033408 A1 | 2/2008 | Bueler et al. |
| 2008/0058778 A1 | 3/2008 | Liedel et al. |

\* cited by examiner

SYSTEMS AND METHODS FOR CORRECTING HIGH ORDER ABERRATIONS IN LASER REFRACTIVE SURGERY

This application is a continuation of U.S. patent application Ser. No. 10/825,864, filed Apr. 16, 2004, which claims the benefit of U.S. Provisional Patent Application No. 60/463,873, filed Apr. 18, 2003, the entire disclosures of which are incorporated hereby by reference for all purposes.

BACKGROUND OF THE INVENTION

To some degree, all eyes deviate from a perfect optical system. These deviations, or aberrations, include imperfections, irregularities, or distortions of the optical quality of the eye, and can lead to refractive or visual errors. Aberrations can be classified into low order and high order aberrations, and can be described mathematically, for example, by Zernike polynomials.

Low order aberrations include prismatic, spherical, and cylindrical errors. First order, or prismatic, errors include vertical prism and horizontal prism errors. Second order, or defocus and astigmatism, errors include myopia, hyperopia, 45/135 astigmatism, and 90/180 astigmatism, for example. Traditional forms of optical correction involve measuring low order aberrations and prescribing sphero-cylindrical lenses in the form of glasses, contact lenses, and refractive surgery.

High order aberrations, on the other hand, are aberrations of the optical system that go beyond nearsightedness, farsightedness, and astigmatism. For example, third order aberrations include trefoil and coma. Fourth order aberrations include $Z(4,-4)$, $Z(4,-2)$, spherical aberration, $Z(4,2)$, and $Z(4,4)$ errors. Generally, high order aberrations include third order errors and above. Such aberrations are typically not corrected with glasses or contact lenses. High order optical errors of the human eye can be responsible for reduced visual acuity in spite of an optimal spherical or cylindrical refraction.

Wavefront-guided refractive surgery provides one method for measuring and treating low order and high order optical distortions in the eye. Wavefront systems measure how light is distorted as it passes into the eye and then is reflected back. An optical map of the eye can be created, detailing specific imperfections. There are several ways of analyzing the optical system of the eye using wavefront technology. One of the more common approaches involves the Hartmann-Shack wavefront sensing method.

Refractive surgery, including wavefront-guided custom ablation treatment, is effective in laser vision correction. However, current systems and methods may be less than ideal, and may even introduce or amplify high order aberrations. In light of the above, it would be desirable to have improved methods, devices, and systems that reduce optical aberrations or inhibit refractive surgery induced aberrations. Relatedly, it would be desirable to have improved methods, devices, and systems that determine, predict, or otherwise characterize optical aberrations or refractive surgery induced aberrations.

BRIEF SUMMARY OF THE INVENTION

The present invention provides a novel approach to evaluating and improving refractive surgery systems. Further, the present invention provides novel approaches to error source control and adjustment or optimization of ablation profiles or other optical data, for addressing high order aberrations. Relatedly, the present invention provides a novel simulation approach to identifying and characterizing system factors that can contribute to, or that can be adjusted to inhibit, optical aberrations. What is more, the present invention provides an approach to modeling limitations on system components so that adjustment of the system parameters such as, for example, the accuracy of registration, the accuracy of fitting in the ablation algorithm, the tracker speed, the accuracy and system latency time of tracking, and/or the laser beam uniformity and variability can be obtained for a certain level of high order aberration correction.

In a first aspect, the invention provides a method of inhibiting an induced aberration resulting from refractive surgery. Typically, the method can include inputting a target optical surface shape; determining a model optical surface shape based on the target optical surface shape and a set of refractive surgery system parameters; comparing the target optical surface shape and the model optical surface shape to determine an aberration induced by the set of refractive surgery system parameters; and adjusting the set of refractive surgery system parameters so as to inhibit the induced aberration. The set of refractive surgery system parameters can include at least one member selected from the group consisting of a wavefront device variable, a laser ablation profile variable, a laser registration and tracking system variable, a microkeratome variable, and a healing effect variable. The adjustment of the set of refractive surgery system parameters can be based on a metric selected from the group consisting of an accuracy variable, a heating variable, and a treatment time variable. The accuracy variable can be based on a root mean squares error factor, the heating variable can be based on a temperature factor, and the treatment time variable can be based on an ablation time factor.

In some aspects, the aberration may include a high order aberration. In other aspects, the target optical surface shape can be configured to address a low order aberration. The wavefront device variable can include a member selected from the group consisting of a spot identification factor, an accommodation factor, and a reconstruction factor. The reconstruction factor can include a member selected from a group consisting of uncompensated residual error portion, a measurement error portion, and a remaining error portion. The laser ablation profile variable can include a member selected from the group consisting of a pulse size factor, a spot size variability factor, a beam uniformity factor, and a laser pulse repetition rate factor. The microkeratome variable can include a member selected from the group consisting of a central flattening and peripheral thickening effect factor and a hinge effect factor. The laser registration and tracking system variable can include a member selected from the group consisting of a registration factor, a linear tracking factor, and a torsional tracking factor. In some aspects, the wavefront device variable can be configured to address a high order aberration. The wavefront device variable can include a gridsize factor adjusted to about 100 μm, and the laser ablation profile variable can include a flying spot scanning factor adjusted to range from about 1 mm to about 1.6 mm. The flying spot scanning factor can be adjusted to about 1.5 mm. The wavefront device variable can include a spot identification error adjusted to about 0.05 microns. The wavefront device variable can include a wavefront reconstruction error adjusted to about 0.05 microns. Similarly, the wavefront device variable can include an accommodation error adjusted to about 0.25D, equivalent to about 0.325 microns RMS error for an approximately 6 mm pupil.

In some related aspects, the microkeratome variable can include an induced positive spherical aberration adjusted to between about 0.1 microns and about 0.3 microns. The microkeratome variable can include a coma in the direction of the microkeratome hinge adjusted to between 0.1 microns and 0.3 microns. The healing effect variable can include a Gaussian kernel adjusted to about 2 micron in height and about 0.5 mm in full width at half maximum (FWHM).

In other related aspects, the set of refractive surgery system parameters can be adjusted such that a post-operative total high order RMS of about 0.3 µm is achieved. In some aspects, the pre-operative total high order RMS may be about 0.3 µm. In some aspects, each component of the total high order RMS does not exceed about 0.113 µm. The set of refractive surgery system parameters can be adjusted such that a post-operative total high order RMS of about 0.1 µm is achieved. In some aspects, each component of the total high order RMS does not exceed about 0.038 µm.

In still other aspects, the laser ablation profile variable can include a variable spot scanning factor, and the laser registration and tracking system variable can include a registration accuracy adjusted to less than about 10 µm in both the vertical and horizontal directions and a rotational error adjusted to less than about 0.5°. The laser ablation profile variable can include a flying spot scanning factor, and the laser registration and tracking system variable can include a registration accuracy adjusted to less than about 10 µm in both the vertical and horizontal directions and a rotational error adjusted to less than about 0.5°. The laser ablation profile variable can include a variable spot scanning factor, and the laser registration and tracking system variable can include a tracking accuracy adjusted to less than about 20 µm in both the vertical and horizontal directions, a latency time adjusted to less than about 10 ms, and a tracking speed adjusted to about 60 Hz or greater. The laser ablation profile variable can include a flying spot scanning factor, and the laser registration and tracking system variable can include a tracking accuracy adjusted to less than about 5 µm in both the vertical and horizontal directions, a latency time adjusted to less than 5 ms, and a tracking speed adjusted to about 200 Hz or greater. The laser ablation profile variable can include a variable spot scanning factor, and the laser registration and tracking system variable can include a cyclo-torsional tracking angular accuracy adjusted to 0.5° or better. The laser ablation profile variable can include a flying spot scanning factor, and the laser registration and tracking system variable can include a cyclo-torsional tracking angular accuracy adjusted to 0.25° or better. The laser ablation profile variable can include a variable spot scanning factor, and the laser registration and tracking system variable can include a laser energy fluctuation adjusted to less than 4%. The laser ablation profile variable can include a flying spot scanning factor, and the laser registration and tracking system variable can include a laser energy fluctuation adjusted to less than 2%.

In some embodiments, the target optical surface shape can include a set of 6-order Zernike polynomials, and the set of refractive surgery system parameters is adjusted such that each component of a post-operative total high order RMS does not exceed about 0.022 µm. The target optical surface shape can include a set of 6-order Zernike polynomials, and the set of refractive surgery system parameters is adjusted such that each component of a post-operative total high order RMS does not exceed about 0.0073 µm.

In some embodiments, the set of refractive surgery system parameters can be adjusted such that a post-operative total high order RMS is substantially equivalent to a pre-operative total high order RMS. The set of refractive surgery system parameters can be adjusted such that a post-operative total high order RMS is less than a pre operative total high order RMS. The set of refractive surgery system parameters can be adjusted such that a post-operative total high order RMS is about one third the amount of a pre operative total high order RMS.

In a second aspect, the present invention can provide a method of altering aberration distribution resulting from optical surface refractive surgery. The method can include inputting a target optical surface shape; determining a model optical surface shape based on the target optical surface shape and a set of refractive surgery system parameters; comparing the target optical surface shape and the model optical surface shape to determine an aberration distribution; and adjusting the set of refractive surgery system parameters so as to alter the aberration distribution.

In a third aspect, the present invention can provide a method of inhibiting a refractive surgery induced aberration. The method can include inputting a target optical surface shape; determining a model optical surface shape based on the target optical surface shape and a set of refractive surgery system parameters, the model optical surface shape having an aberration; and adjusting the set of refractive surgery system parameters so as to inhibit the aberration.

In a fourth aspect, the present invention can provide a system for inhibiting an induced aberration resulting from refractive surgery. The system can include an input that accepts a target optical surface shape; a module that determines a model optical surface shape based on the target optical surface shape and a set of refractive surgery system parameters; and a module that adjusts the set of refractive surgery system parameters so as to inhibit an aberration in the model optical surface shape. The set of refractive surgery system parameters can include at least one member selected from the group consisting of a wavefront device variable, a laser ablation profile variable, a laser registration and tracking system variable, a microkeratome variable, and a healing effect variable. The module that adjusts the refractive surgery system parameters can include a metric selected from the group consisting of an accuracy variable, a heating variable, and a treatment time variable. The accuracy variable can be based on a root mean squares error factor, the heating variable can be based on a temperature factor, and the treatment time variable can be based on an ablation time factor.

In some aspects, the aberration may include a high order aberration. In other aspects, the target optical surface shape can be configured to address a low order aberration. The wavefront device variable can include a member selected from the group consisting of a spot identification factor, an accommodation factor, and a reconstruction factor. The reconstruction factor can include a member selected from a group consisting of uncompensated residual error portion, a measurement error portion, and a remaining error portion. The laser ablation profile variable can include a member selected from the group consisting of a pulse size factor, a spot size variability factor, a beam uniformity factor, and a laser pulse repetition rate factor. The microkeratome variable can include a member selected from the group consisting of a central flattening and peripheral thickening effect factor and a hinge effect factor. The laser registration and tracking system variable can include a member selected from the group consisting of a registration factor, a linear tracking factor, and a torsional tracking factor. In some aspects, the wavefront device variable can be configured to address a high order aberration. The wavefront device variable can include a gridsize factor adjusted to about 100 µm, and the laser ablation profile variable can include a flying spot scanning factor adjusted to range from about 1 mm to about 1.6 mm. The flying spot scanning factor can be adjusted to about 1.5 mm. The wavefront device variable can include a spot identification error adjusted to about 0.05 microns. The wavefront device variable can include a wavefront reconstruction error adjusted to about 0.05 microns. Similarly, the wavefront device variable can include an accommodation error adjusted to about 0.25D, equivalent to about 0.325 microns RMS error for an approximately 6 mm pupil.

In some related aspects, the microkeratome variable can include an induced positive spherical aberration adjusted to between about 0.1 microns and about 0.3 microns. The microkeratome variable can include a coma in the direction of the microkeratome hinge adjusted to between 0.1 microns and 0.3 microns. The healing effect variable can include a Gaussian kernel adjusted to about 2 micron in height and about 0.5 mm in full width at half maximum (FWHM).

In other related aspects, the set of refractive surgery system parameters can be adjusted such that a post-operative total high order RMS of about 0.3 µm is achieved. In some aspects, the pre-operative total high order RMS may be about 0.3 µm. In some aspects, each component of the total high order RMS does not exceed about 0.113 µm. The set of refractive surgery system parameters can be adjusted such that a post-operative total high order RMS of about 0.1 µm is achieved. In some aspects, each component of the total high order RMS does not exceed about 0.038 µm.

In still other aspects, the laser ablation profile variable can include a variable spot scanning factor, and the laser registration and tracking system variable can include a registration accuracy adjusted to less than about 10 µm in both the vertical and horizontal directions and a rotational error adjusted to less than about 0.5°. The laser ablation profile variable can include a flying spot scanning factor, and the laser registration and tracking system variable can include a registration accuracy adjusted to less than about 10 µm in both the vertical and horizontal directions and a rotational error adjusted to less than about 0.5°. The laser ablation profile variable can include a variable spot scanning factor, and the laser registration and tracking system variable can include a tracking accuracy adjusted to less than about 20 µm in both the vertical and horizontal directions, a latency time adjusted to less than about 10 ms, and a tracking speed adjusted to about 60 Hz or greater. The laser ablation profile variable can include a flying spot scanning factor, and the laser registration and tracking system variable can include a tracking accuracy adjusted to less than about 5 µm in both the vertical and horizontal directions, a latency time adjusted to less than 5 ms, and a tracking speed adjusted to about 200 Hz or greater. The laser ablation profile variable can include a variable spot scanning factor, and the laser registration and tracking system variable can include a cyclo-torsional tracking angular accuracy adjusted to 0.5° or better. The laser ablation profile variable can include a flying spot scanning factor, and the laser registration and tracking system variable can include a cyclo-torsional tracking angular accuracy adjusted to 0.25° or better. The laser ablation profile variable can include a variable spot scanning factor, and the laser registration and tracking system variable can include a laser energy fluctuation adjusted to less than 4%. The laser ablation profile variable can include a flying spot scanning factor, and the laser registration and tracking system variable can include a laser energy fluctuation adjusted to less than 2%.

In some embodiments, the target optical surface shape can include a set of 6-order Zernike polynomials, and the set of refractive surgery system parameters is adjusted such that each component of a post-operative total high order RMS does not exceed about 0.022 µm. The target optical surface shape can include a set of 6-order Zernike polynomials, and the set of refractive surgery system parameters is adjusted such that each component of a post-operative total high order RMS does not exceed about 0.0073 µm.

In some embodiments, the set of refractive surgery system parameters can be adjusted such that a post-operative total high order RMS is substantially equivalent to a pre-operative total high order RMS. The set of refractive surgery system parameters can be adjusted such that a post-operative total high order RMS is less than a pre operative total high order RMS. The set of refractive surgery system parameters can be adjusted such that a post-operative total high order RMS is about one third the amount of a pre operative total high order RMS.

These and other aspects will be apparent in the remainder of the figures, description, and claims.

DETAILED DESCRIPTION OF THE INVENTION

The present invention can be readily adapted for use with existing laser systems, wavefront measurement systems, and other optical measurement devices. While the systems, software, and methods of the present invention are described primarily in the context of a laser eye surgery system, it should be understood the present invention may be adapted for use in alternative eye treatment procedures and systems such as spectacle lenses, intraocular lenses, contact lenses, corneal ring implants, collagenous corneal tissue thermal remodeling, and the like.

Figure 1:
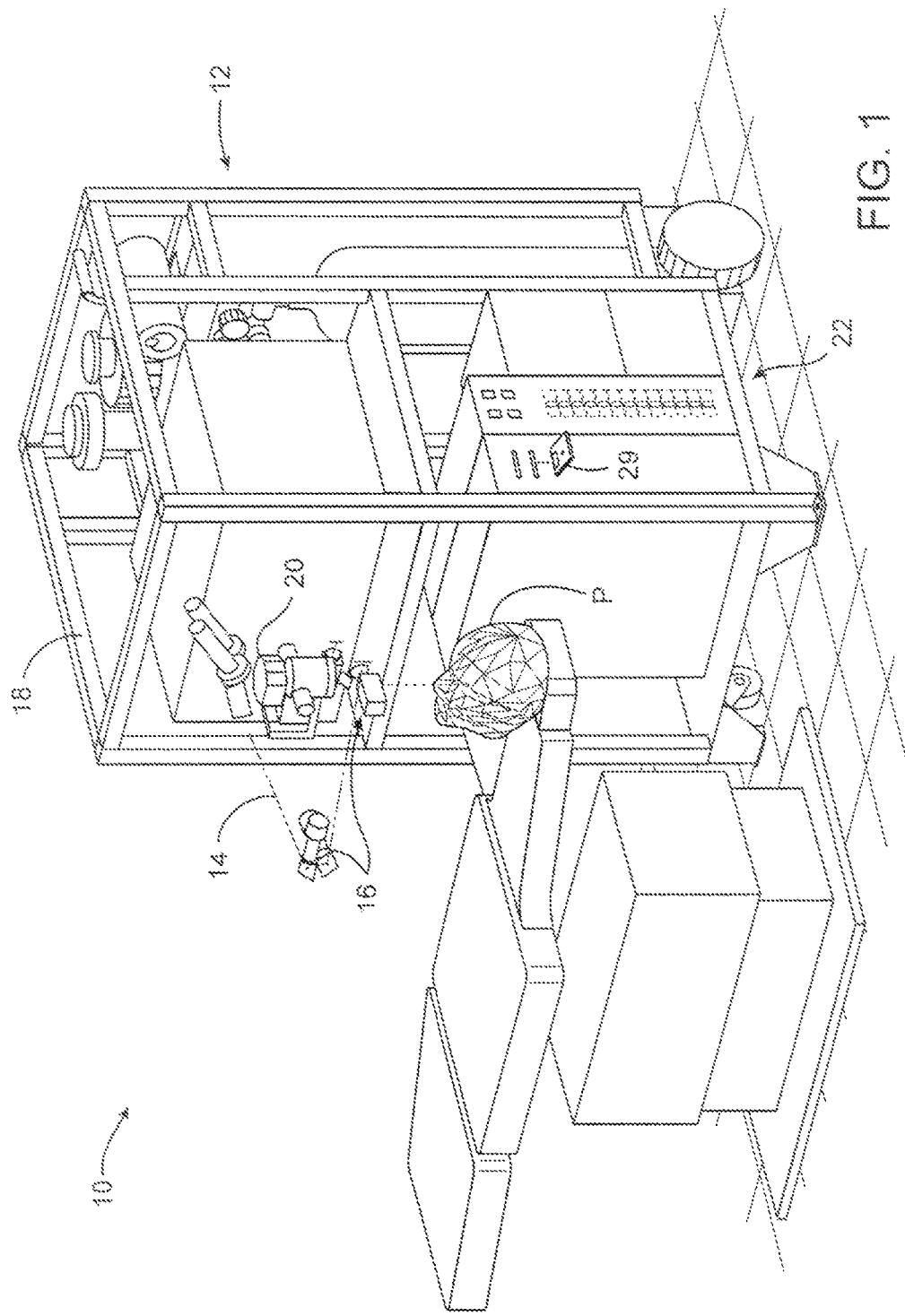
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
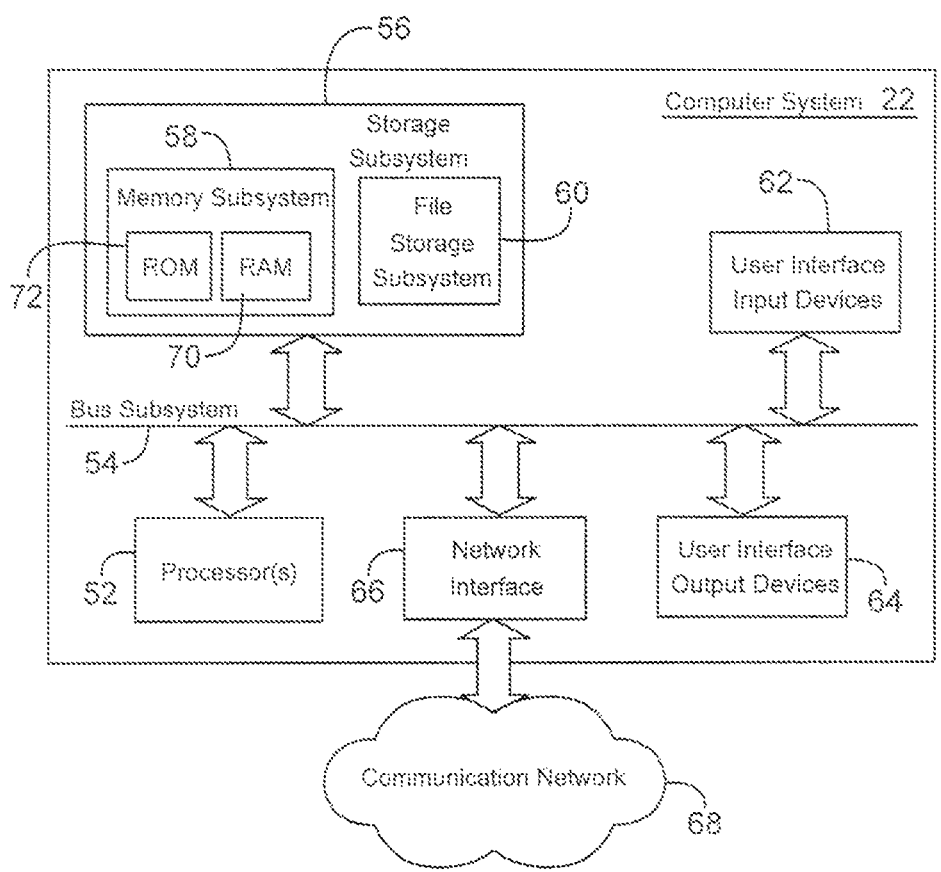
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
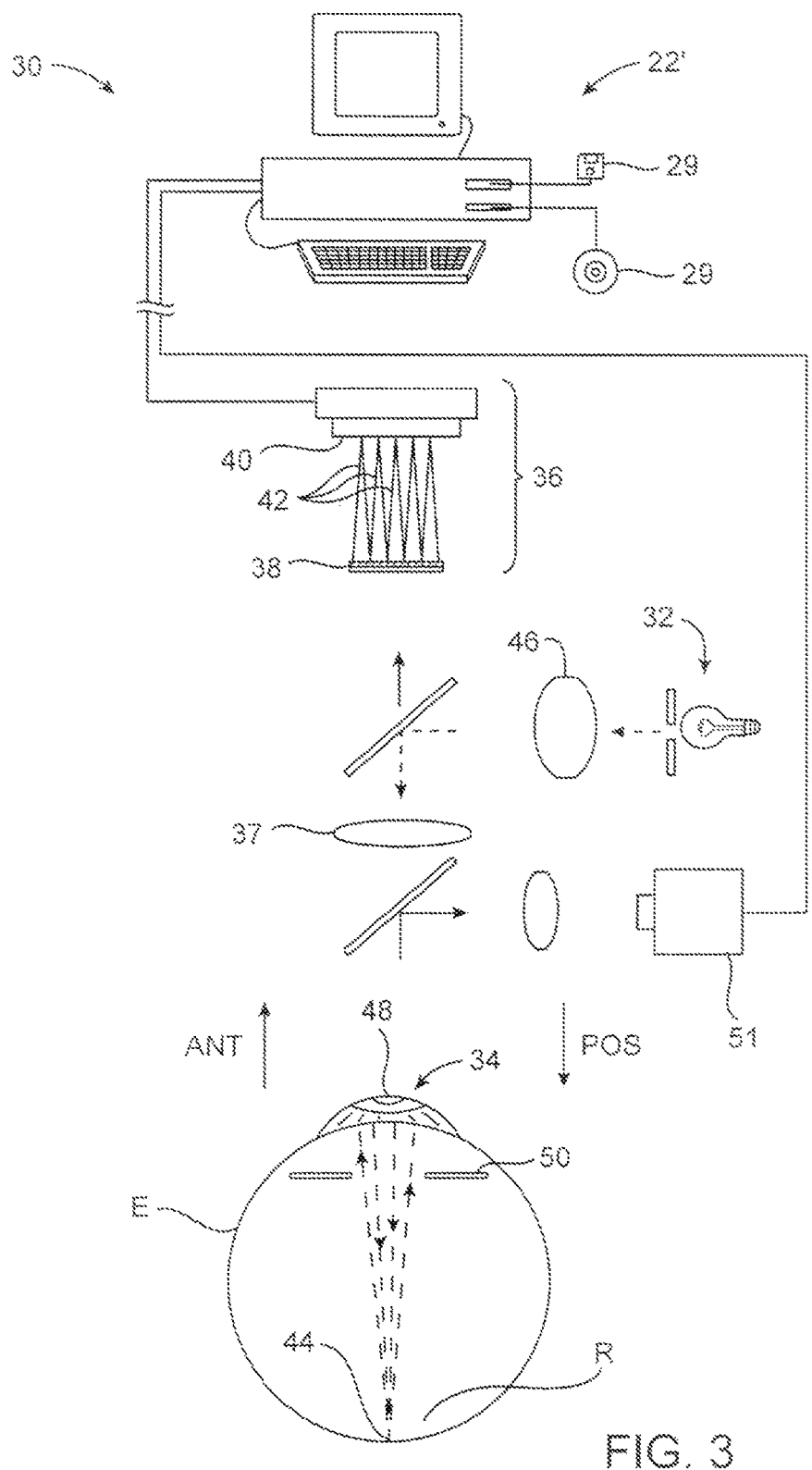
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
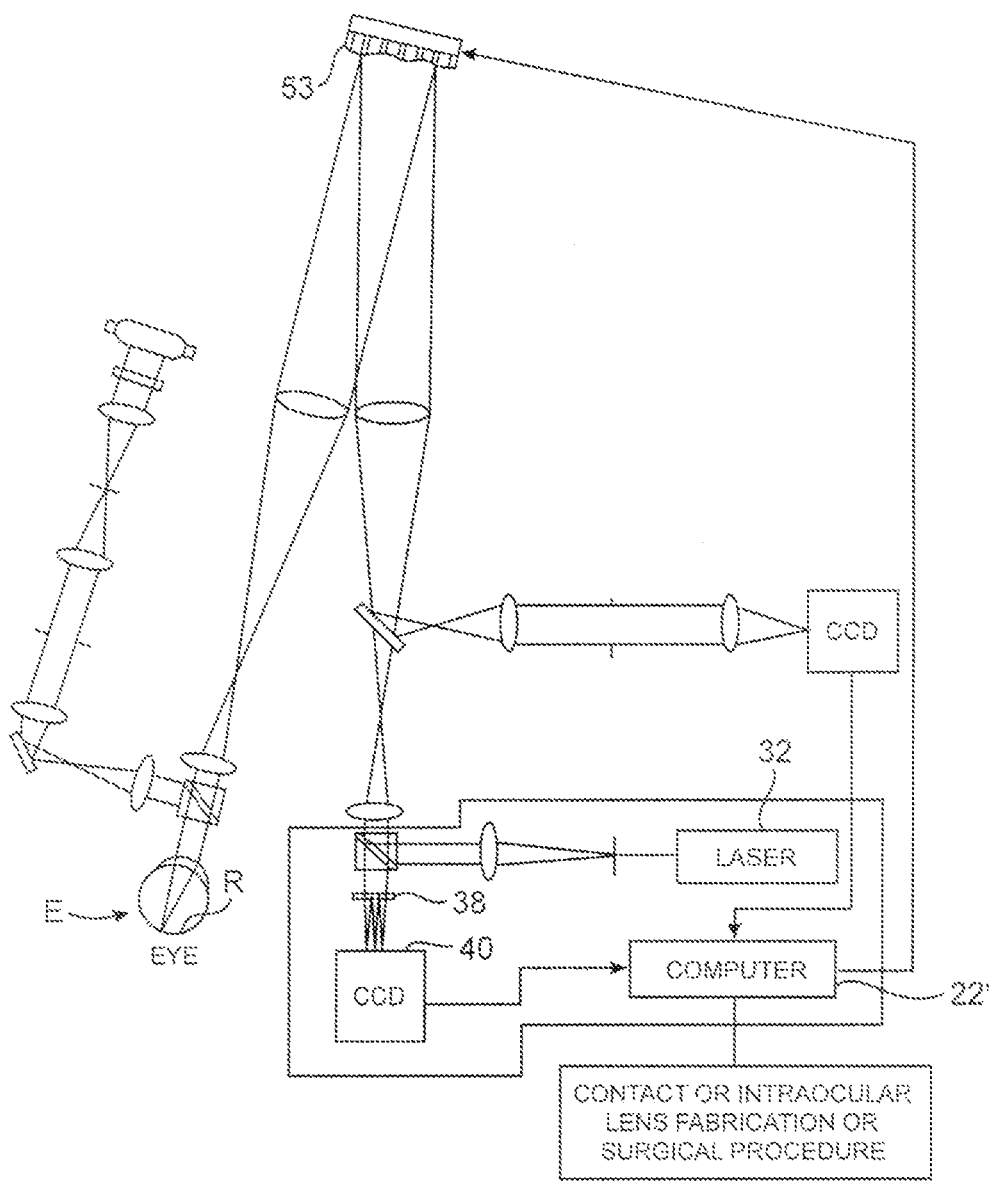
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a VISX WaveScan®, available from VISX, INCORPORATED of Santa Clara, Calif. One embodiment includes a WaveScan® with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention.

I. Target Optical Surface Shape

Refractive surgery is typically based on a target optical surface shape that is selected or determined to treat a vision condition in a patient. A target optical surface shape can be based on or represented by any of a variety of target optical surface shape data or data formats. In this context, a vision condition can be analogous to a refractive case. Examples of refractive cases include the following.

| Refractive Case | Optical Zone × Ablation Zone |
|---|---|
| 1. Myopic (−4D) | 6 mm × 8 mm |
| 2. Hyperopic (+2D) | 5 mm × 9 mm |
| 3. Myopic Astigmatism (−2DS/−1DC × 34°) | 6 mm × 8 mm |
| 4. Hyperopic Astigmatism (+2DS/−1DC × 65°) | 5 mm × 9 mm |
| 5. Mixed Astigmatism (+2DS/−3DC × 45°) | 5 mm × 9 mm |
| 6. Therapeutic (+2.35DS/−3.51DC × 17°) | 6 mm × 8 mm |

Figure 8:
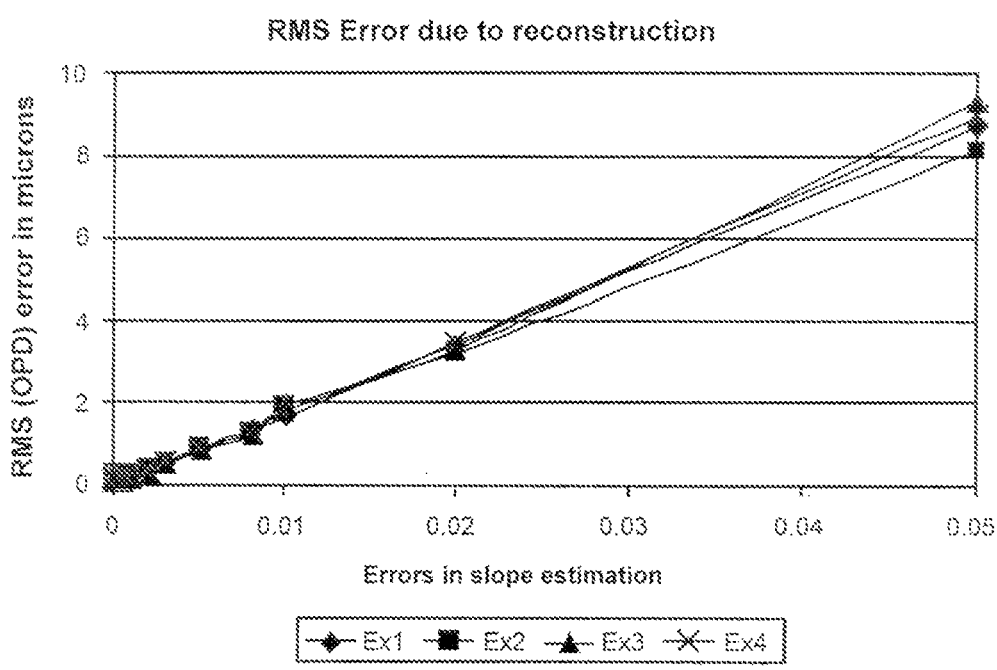
FIG. 8 illustrates RMS error due to reconstruction according to an embodiment of the present invention.
Figure 8A:
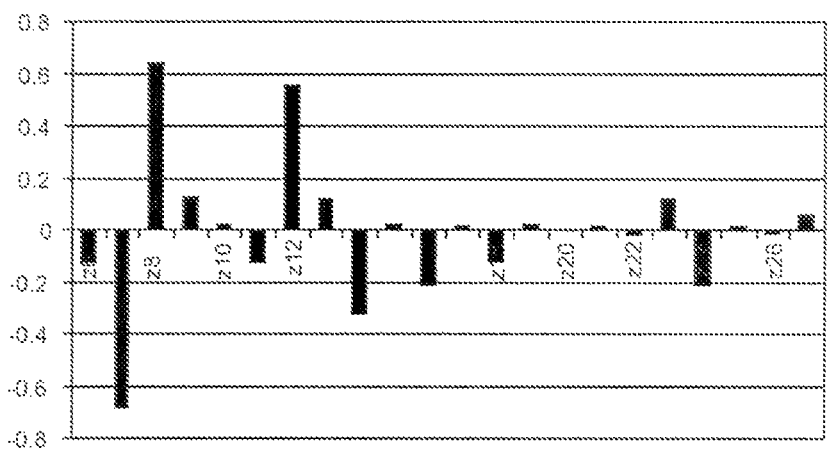
FIG. 8A illustrates high order aberrations of a therapeutic eye according to an embodiment of the present invention.

Refractive cases 1 through 5 represent hypothetical refractive cases, and the therapeutic eye of case 6 represents a real eye case having more than a 1 μm high order aberration RMS with large coma and spherical components (for example a single high order Zernike mode $Z_8^8$, or Z45, with 1 μm RMS error). The optical zone can be based on a hypothetical pupil diameter. In the real eye case, the optical zone can correspond to a pupil diameter under standard lighting conditions used during wavefront evaluation. The high order part of the exemplary therapeutic eye refractive case is shown in FIG. 8A. In one embodiment of the present invention, the target optical surface shape includes a set of 6-order Zernike polynomials.

Figure 4:
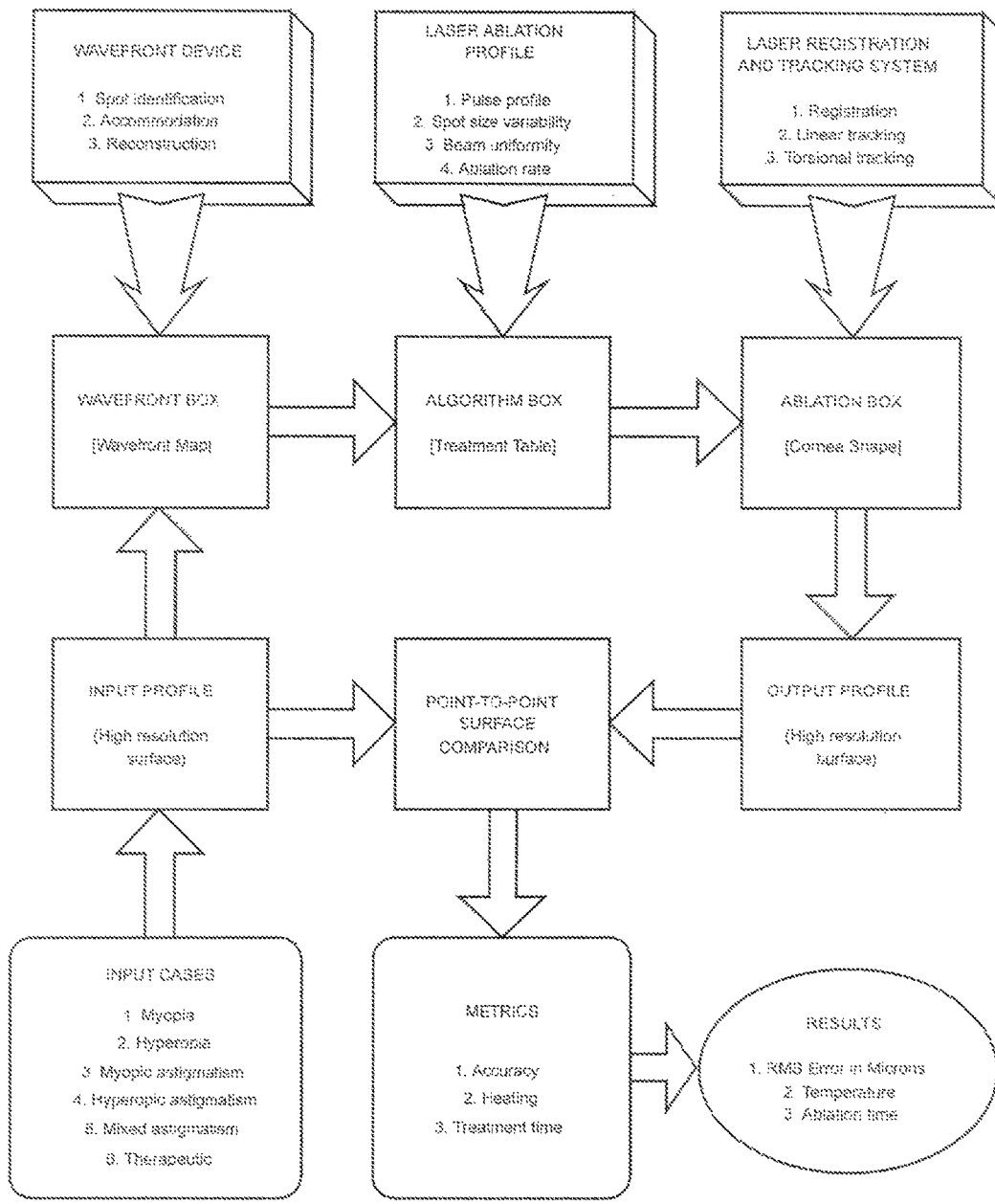
FIG. 4 illustrates a system flow diagram according to an embodiment of the present invention.

Refractive cases such as these can be determined with a wavefront sensing device, which can determine both low and high order aberrations. In some cases, the target optical surface shape can be configured to address a low order aberration. Some refractive cases may present both low and high order aberrations, and may benefit from a combined target optical surface shape treatment. As shown in FIG. 4, given a particular vision condition or refractive case, it is possible to generate a corresponding high resolution target optical surface shape, or input profile, for treating the condition.

II. Refractive Surgery System Parameters

Given a target optical surface shape, it is possible to determine a model optical surface shape based on the target shape and a set of refractive surgery system parameters. The refractive surgery system parameters correspond to the individual system components of the system. For example, as shown in FIG. 4, one embodiment of the refractive surgery system can include components such as a wavefront device, a laser ablation profile, and a laser-servo system such as a laser registration and tracking system. These components can introduce errors into the model optical surface shape. The surgery system can have error sources including, for example, a wavefront device measurement error, a wavefront surface fitting error or algorithm imperfection, a laser beam uniformity and variability error, a registration error, and a tracking error. Thus, the model surface shape can include aberrations that are introduced or amplified by the surgery system parameters, and these aberrations can be described and evaluated by certain mathematical equations.

Figure 5:
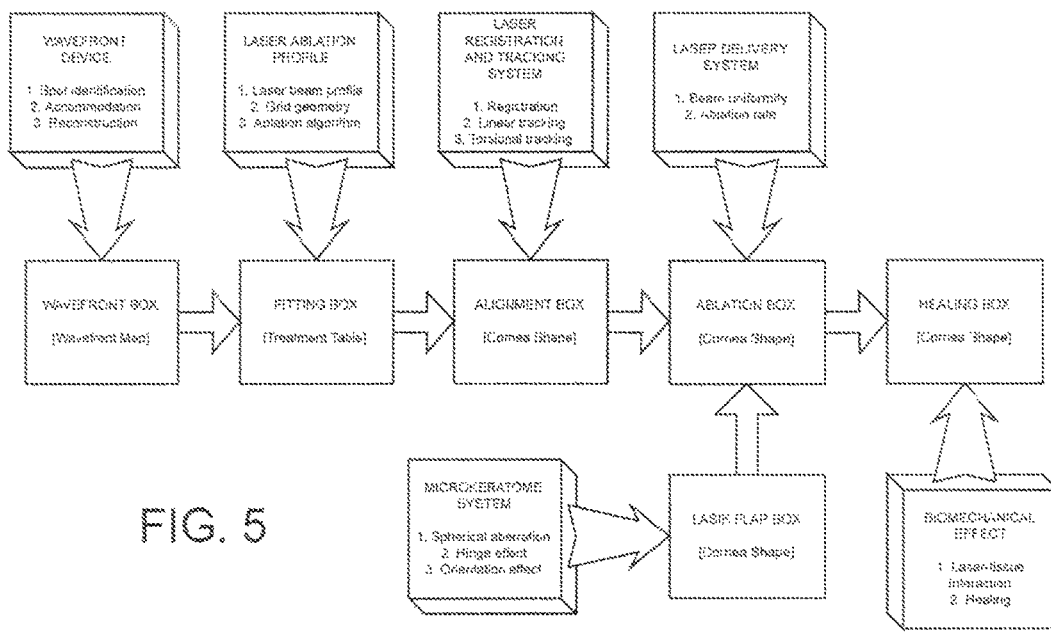
FIG. 5 illustrates a system flow diagram according to an embodiment of the present invention.

FIG. 5 illustrates another embodiment of an overall refractive system according to the present invention, which can include components such as a wavefront device, a laser ablation profile, a laser registration and tracking system, and a laser delivery system. Such a refractive surgery system can have error sources including, for example, a wavefront device measurement error, a laser beam profile error, a laser registration and tracking system error, and a laser delivery system error. Accordingly, a set of refractive surgery system parameters can be selected from the group consisting of a wavefront device variable, a laser ablation profile variable, a laser registration and tracking system variable, a biomechanical variable, and a healing effect variable.

As noted above, different components of the refractive surgery system, as represented by the surgery system parameters, can by their own accord introduce different errors or aberrations into the model optical surface shape, and they can exacerbate different errors or aberrations present in the target optical surface shape. Consequently, there may be different RMS values or other error values associated with the different system components. The present invention provides a numerical approach to characterizing or identifying error sources in such a system.

To evaluate the error sources, it is helpful to consider the overall system. Assuming that all of the error sources are statistically independent, the overall error associated with the system embodiment shown in FIG. 4 can be represented as $$\Delta = \sigma_{WF}^2 + \sigma_{AB}^2 + \sigma_{RT}^2 \qquad (1)$$

where $\sigma_{WF}^2$ represents a WF (wavefront) measurement induced error or variance, $\sigma_{AB}^2$ represents an ablation profile related variance or fitting error, and $\sigma_{RT}^2$ represents a laser system registration and tracking error or variance. This total error is a representation of the system source errors that can contribute aberrations to a model optical surface shape.

In another example, the total error associated with the surgical system parameters can be written as $$\sigma_{total}^2 = \sigma_w^2 + \sigma_f^2 + \sigma_r^2 + \sigma_t^2 + \sigma_b^2 \qquad (2)$$

where $\sigma_w^2$ represents a measurement error in the wavefront device, $\sigma_f^2$ represents an error induced in surface fitting with respect to a certain algorithm such as a simulated annealing algorithm, $\sigma_r^2$ represents an error induced by registration, $\sigma_t^2$ represents a tracking error, and $\sigma_b^2$ represents an error due to laser beam uniformity and variability.

As shown in FIG. 5, another exemplary surgical system can include a wavefront device, a laser ablation profile, a laser registration and tracking component, and a laser delivery system. As indicated in the figure, errors introduced by a microkeratome can also be factored into the total system error analysis. When assuming that all the error sources are statistically independent, the overall error can be represented as $$\sigma_{total}^2 = H(\sigma_w^2 + \sigma_f^2 + \sigma_r^2 + \sigma_t^2 + \sigma_b^2 + \sigma_m^2), \qquad (3)$$

where $H(\bullet)$ represents a non-linear healing operator, $\sigma_w^2$ represents a total error in the wavefront device, $\sigma_f^2$ represents an error induced in surface fitting with respect to a certain algorithm such as a simulated annealing algorithm, $\sigma_r^2$ represents an error induced by the registration, $\sigma_t^2$ represents a tracking error, $\sigma_b^2$ represents an error due to laser beam uniformity and variability, and $\sigma_m^2$ represents an error induced from the LASIK flap, or biomechanical effect. The individual error sources are discussed in further detail below.

In some embodiments, the set of refractive surgery system parameters can be adjusted such that a post-operative total high order RMS is substantially equivalent to a pre-operative total high order RMS. In other embodiments, the set of refractive surgery system parameters can be adjusted such that a post-operative total high order RMS is less than a pre operative total high order RMS. In still other embodiments, the set of refractive surgery system parameters can be adjusted such that a post-operative total high order RMS is about one third the amount of a pre operative total high order RMS.

The set of refractive surgery system parameters can be adjusted such that a post-operative total high order RMS of about 0.1 μm to about 0.3 μm is achieved. In related embodiments, the set of refractive surgery system parameters can be adjusted such that each system component of the total high order RMS does not exceed from about 0.038 μm to about 0.113 μm. In other embodiments, where the total RMS error is about 0.1 μm to about 0.3 μm and the system includes 3 components, the set of refractive surgery system parameters can be adjusted such that each system component of the total high order RMS does not exceed from about 0.0577 μm to about 0.173 μm. In yet other embodiments, where the total RMS error is about 0.1 μm to about 0.3 μm and the system includes 10 components, the set of refractive surgery system parameters can be adjusted such that each system component of the total high order RMS does not exceed from about 0.0316 μm to about 0.0949 μm.

In one embodiment of the present invention, the target optical surface shape includes a set of 6-order Zernike polynomials, and the set of refractive surgery system parameters is adjusted such that each component of a post-operative total high order RMS does not exceed about 0.022 μm. In another embodiment, the target optical surface shape includes a set of 6-order Zernike polynomials, and the set of refractive surgery system parameters is adjusted such that each component of a post-operative total high order RMS does not exceed about 0.0073 μm. In other embodiments, where the total RMS error is about 0.1 μm to about 0.3 μm and the system includes 3 components, the set of refractive surgery system parameters can be adjusted such that each system component of the total high order RMS does not exceed from about 0.0111 μm to about 0.0333 μm. In yet other embodiments, where the total RMS error is about 0.1 μm to about 0.3 μm and the system includes 10 components, the set of refractive surgery system parameters can be adjusted such that each system component of the total high order RMS does not exceed from about 0.0061 μm to about 0.0111 μm.

A. Wavefront Device Parameters

A wavefront device measurement error, which can be represented as $\sigma_w^2$, can originate from errors associated with any of a variety of parameters. For example, as shown in FIGS. 4 and 5, a wavefront device can include parameters such as spot identification (e.g. Hartmann-Shack spot pattern identification), accommodation, and reconstruction. Accordingly, a wavefront device variable can be selected from the group consisting of a spot identification factor, an accommodation factor, and a reconstruction factor. In some cases, the wavefront device variable is configured to address a high order aberration.

1. Accommodation Error

Accommodation error can be due to partial accommodation or micro-accommodation of the patient, which can be translated to a root mean squares (RMS) error. Micro-fluctuation, or accommodation drift, can be present in a patient as they gaze at, but are unable to fixate upon, a distant target. Most patients will accommodate at least slightly, and micro-accommodation corresponds to slight changes in the relaxation of accommodation. To the extent a patient cannot fully relax and therefore accommodates during this procedure, this accommodation can become part of the error. Assuming the random error of accommodation is a for an eye with pupil radius of R, an RMS accommodation error can be expressed as $$\sigma_{ac}^2 = \frac{a^2 R^4}{48}, \qquad (4)$$

where a is given in diopters and R is given in mm. a can represent a variable averaged microaccommodation for several patients being measured.

In a practical clinical setting, it may be difficult to keep the accommodation drift, or accommodation error, under 0.1D. In some cases, accommodation error of more than one diopter has been observed. Taking 0.1D as a limit, the minimum RMS accommodation error for a 6 mm pupil is then 0.15 microns. In some embodiments, the wavefront device variable includes an accommodation error of 0.25D, equivalent to 0.325 microns RMS error for a 6 mm pupil.

Figure 7:
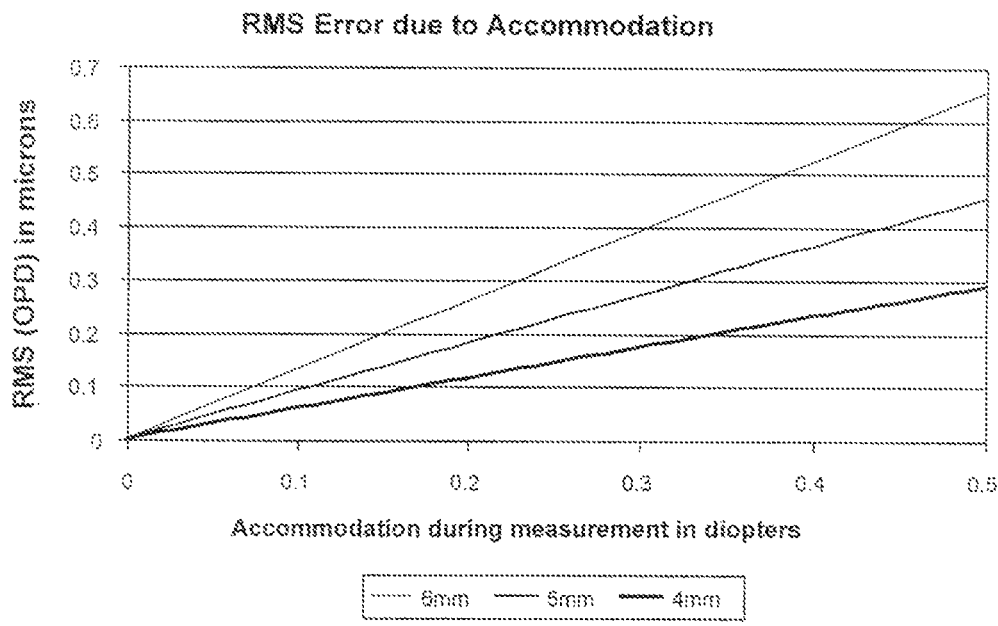
FIG. 7 illustrates RMS error due to accommodation according to an embodiment of the present invention.

For the accommodation error, FIG. 7 shows the contribution of the accommodation error to the total RMS accommodation error for different pupil sizes. It is clear to see that larger pupil sizes correspond with larger total RMS errors when the amount of accommodation remains constant.

2. Reconstruction Error

For the wavefront device error, it is also possible to consider error induced from a wavefront reconstruction error. The sources of a reconstruction error can include an uncompensated error due to truncation of the number of basis functions, such as Zernike polynomials; a measurement error; and a remaining error due to aliasing of the derivatives of basis functions. A complete theoretical analysis is given by Dai, in "Modal wave-front reconstruction with Zernike polynomials and Karhunen-Loève functions," *J. Opt. Soc. Am. A* 13, 1218-1225 (1996), which is incorporated herein by reference in its entirety for all purposes. In one embodiment, the reconstruction error can be written as $$\sigma_{rc}^2 = \sigma_{uc}^2 + \sigma_{sp}^2 + \sigma_{rs}^2. \tag{5}$$

where $\sigma_{uc}^2$ is this the uncompensated error, $\sigma_{sp}^2$ is this the spot identification error, and $\sigma_{rs}^2$ is this the remaining error.

The uncompensated error may be difficult to estimate due to the lack of statistics of the Zernike expansion for human eye's aberrations. However, a treatment with consideration of the Hartmann-Shack sensor configuration is possible. The measurement error, which is often directly related to spot identification, can be treated as spot identification error. Finally, the remaining error can be small, especially when the number of sub-apertures is relatively small. For example, in one embodiment the VISX WaveScan® device uses 37 sub-apertures.

For a wavefront reconstruction error, it is possible to assume that different error sources result in the final uncertainty in a slope estimate. These error sources include CCD detector noise, noise in pixel round-off position error, as well as error contained in the reconstruction algorithm, and these could affect spot identification error and reconstruction error. FIG. 8 shows the contribution of slope estimation error to the total RMS error for four example cases, illustrating that an error in slope estimation can affect the total RMS error. In some embodiments, the wavefront reconstruction error can be about 0.05 µm.

A spot identification error can be an error due to round off of pixel position (integer pixel position), low contrast spots due to corneal reflection, or low signal to noise (S/N) ratio. A complete theoretical derivation of the total spot identification error is not given here. It is possible to use a simple Gaussian random noise model for the simulation of spot identification error. However, a general formulation can be given as $$\sigma_{sp}^2 = \sigma_{ro}^2 + \sigma_{sn}^2. \tag{6}$$

where $\sigma_{ro}^2$ is this the round off error and $\sigma_{sn}^2$ is this the signal to noise ratio error. In some embodiments, the spot identification error can be about 0.05 µm.

3. Total Wavefront Device Error

The total wavefront device error can be written as $$\sigma_w^2 = \sigma_{rc}^2 + \sigma_{ac}^2. \tag{7}$$

which in some embodiments is the final formula for RMS calculation for a wavefront device, and reflects the sum of the accommodation error and the reconstruction error.

In one embodiment, a reconstruction error can reflect a typical slope estimation error of 0.001 corresponding to an RMS reconstruction error of about 0.2 microns. In this embodiment, the total RMS error from a wavefront device can be at the order of 0.25 microns, assuming an RMS accommodation error of 0.1 microns.

A large portion of the wavefront device error may often be manifested as errors in low orders, or mostly in the sphere error. Therefore, the end result, or true ablation (e.g. the model optical surface shape) may be a random over correction or under correction. If the total RMS wavefront device error is entirely a low order aberration, it may correspond to a 0.2D refractive error, which can be considered as small. The statistical trend, though, would result in relatively small total RMS wavefront device error. The truly induced high order total RMS error, which typically originates from the system parameters, will often be below 0.1 microns.

One approach to correcting or inhibiting high order aberrations involves controlling the overall wavefront error to a certain limit. For instance, using a 100 µm scanning resolution of a Gaussian spot (FWHM=0.75 mm) to correct a −4DS eye without high order aberrations can induce 0.21 µm high order aberration (HOA). In some embodiments, the wavefront device variable includes a 100 µm gridsize factor.

B. Laser Ablation Profile Parameters

Laser ablation profile errors are sometimes referred to as wavefront surface fitting errors, or algorithm errors. Wavefront surface fitting errors can be the result of a numerical solution of a multi-dimensional problem in fitting individual laser pulses to the expected wavefront surface, or model optical surface shape. Laser ablation profile errors, which can be represented as $\sigma_f^2$, can originate from errors associated with any of a variety of parameters. Accordingly, a laser ablation profile variable can include a pulse size factor, a spot size variability factor, a beam uniformity factor, and a laser pulse repetition rate factor.

In one embodiment of the present invention, as shown in FIG. 4, a laser ablation profile can include parameters such as pulse profile, spot size variability, beam uniformity, and laser pulse repetition rate. In another embodiment of the present invention, as shown in FIG. 5, a laser ablation profile can include parameters such as laser beam profile, grid geometry, and ablation algorithm. In FIG. 5, the beam uniformity and laser pulse repetition rate are characterized as laser delivery system parameters, and are further discussed under that section heading below.

1. Laser Pulse Profile Fitting Errors

Laser ablation pulse profiles can be generated in a variety of ways. In the following examples, the Y(r) function describes how to generate the ablation pulse profile, where σ represents the standard deviation of a Gaussian profile, and FWHM represents the full width at half maximum of the Gaussian profile. Different types of pulse profiles can contribute different amounts of error to the laser ablation profile error. For example, a laser ablation profile variable can include a variable spot scanning factor or a flying spot scanning error.

a. Flying Spot Scanning (FSS) Pulse Profile

Figure 9A:
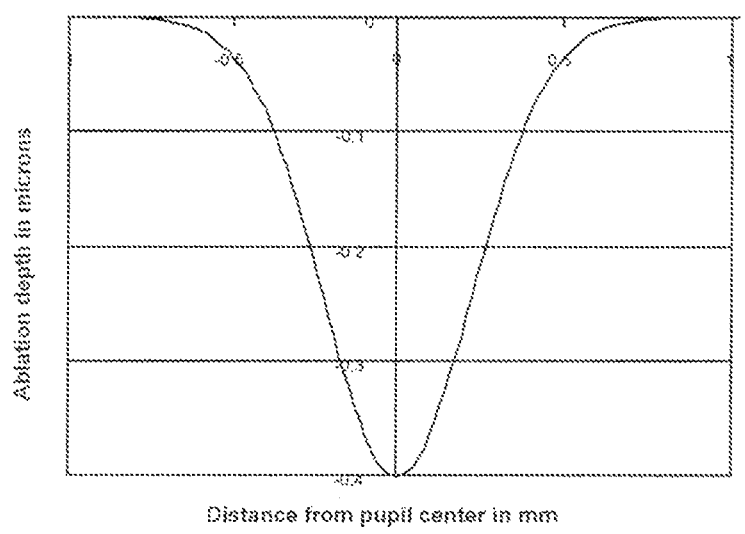
FIG. 9A illustrates a flying spot scanning profile according to an embodiment of the present invention.

A Flying Spot Scanning (FSS) pulse profile can be represented by the following formula:

$$Y(r) = -0.4 \exp[(-8 \ln 2/\sigma^2)(4-r)^2] \tag{8}$$

where σ=D/2 and D is the spot size, and where FWHM is D/√8=0.3536D. Y(r) represents the ablation depth, and r represents the distance from the pupil center, in mm. Thus, for a 0.75 mm FWHM spot, D=2 mm. This profile is depicted in FIG. 9A.

In one embodiment, a −4 Diopter input is used to generate the basis function, or basis data, for a Flying Spot Scanning profile. The following results were obtained: 5481 pulses, PV=1.03 µm, RMS=0.14 µm (OPD), which is the profile fitting error. All measurements are in optical path difference (OPD). PV is a peak to valley measurement, and represents the difference between maximum and minimum in sequence of values. It reflects the magnitude of fluctuation. The RMS is similar to standard deviation. In some embodiments, the flying spot scanning factor can be about 1.5 mm.

b. Variable Spot Scanning (VSS) Pulse Profile

Figure 9B:
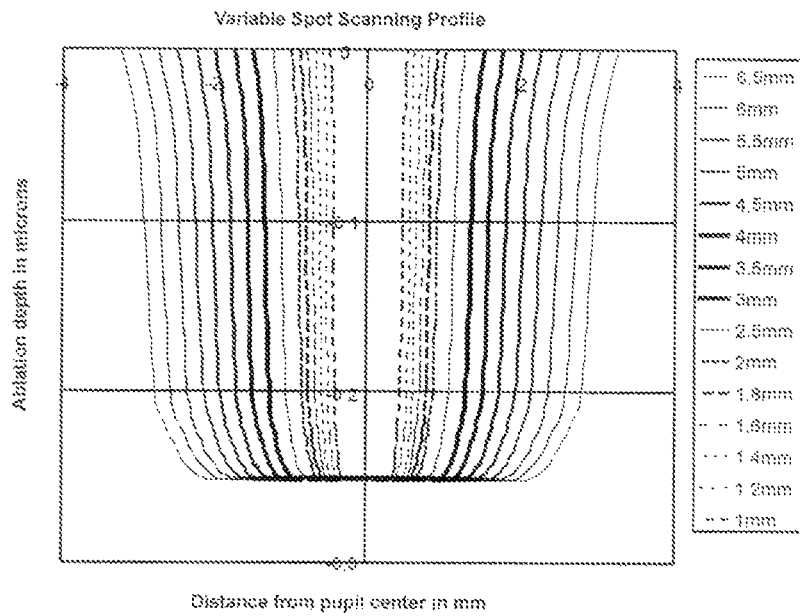
FIG. 9B illustrates a variable spot scanning profile according to an embodiment of the present invention.

In a Variable Spot Scanning (VSS) profile laser, a top hat shape can be used. This profile is depicted in FIG. 9B, at 15 different diameters. In the −4 Diopter input embodiment describe above, for the VISX Variable Spot Scanning profile, the following results were obtained: 339 pulses, PV=0.78 µm, RMS=0.11 µm, which is the profile fitting error. All measurements are in optical path difference (OPD).

c. Comparison Between Various Pulse Profiles

Figure 10A:
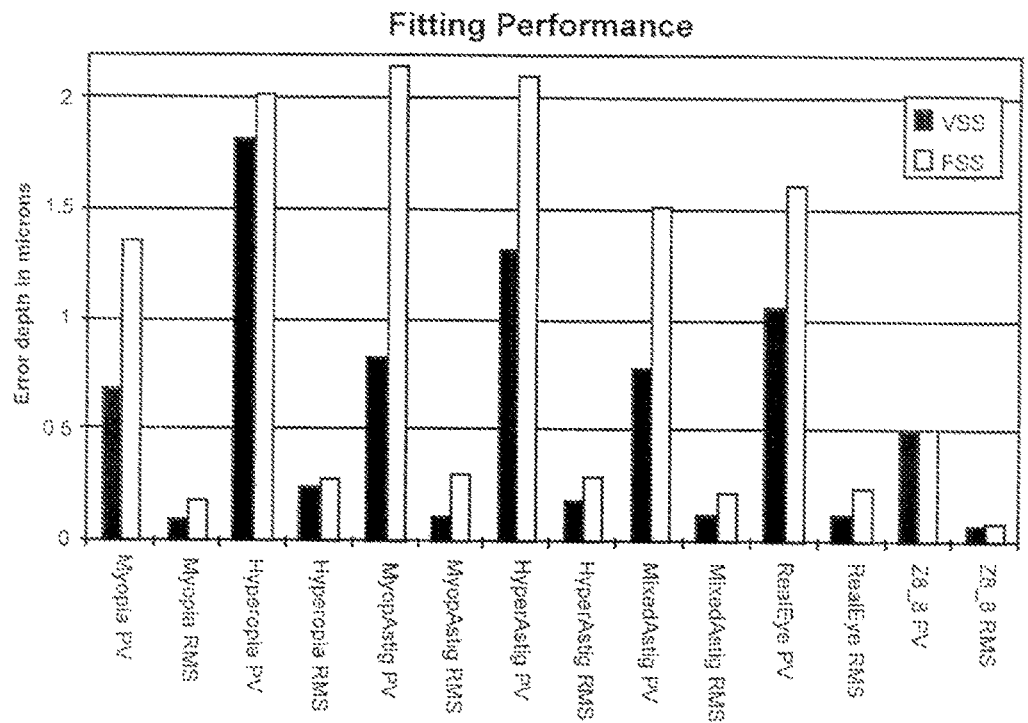
FIG. 10A illustrates fitting performance according to an embodiment of the present invention.

The fitting errors, or $\sigma_f^2$, for the following laser pulse profiles were evaluated with respect to a variety of refractive cases, and the results are shown in FIG. 10A. This assumes that all other laser ablation profile parameters, such as spot size variability and grid geometry, were equal, and there were no other error sources.

2. Spot Size Variability Errors

Figure 12A:
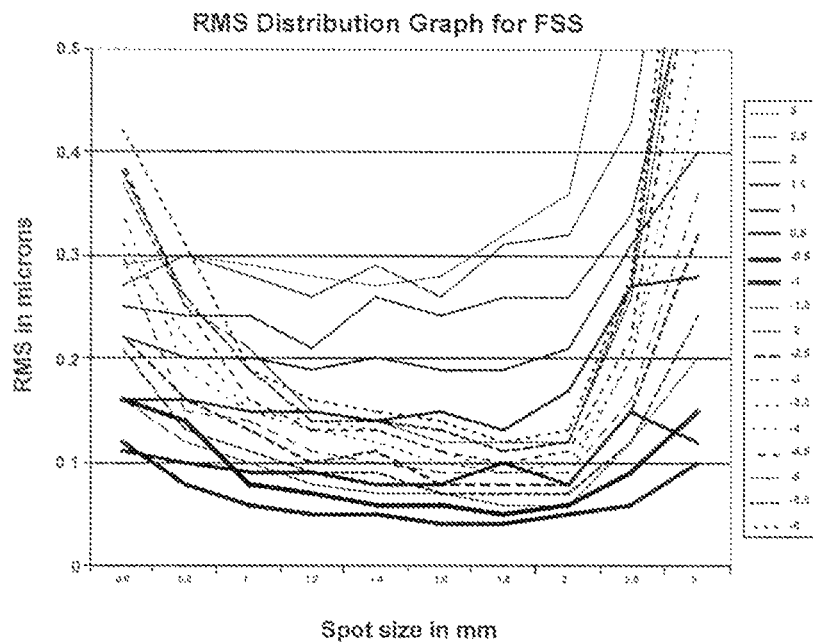
FIG. 12A illustrates an RMS distribution graph for FSS according to an embodiment of the present invention.
Figure 12B:
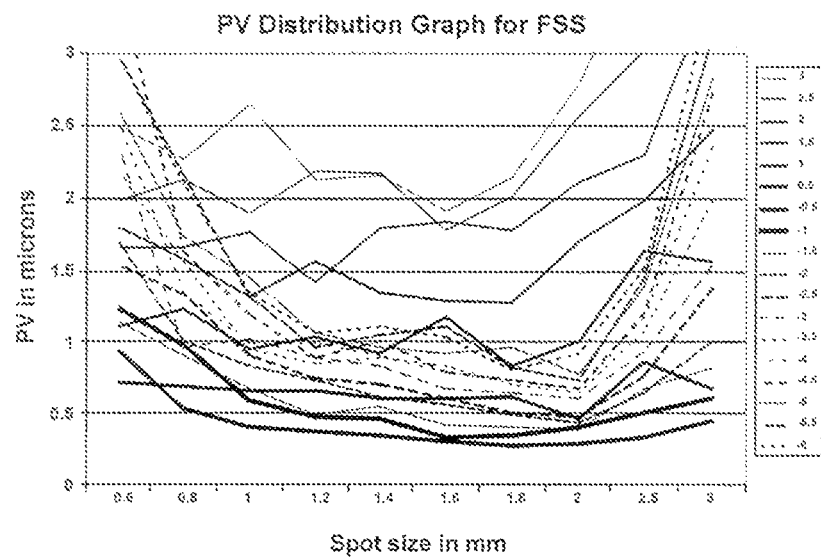
FIG. 12B illustrates a PV distribution graph for FSS according to an embodiment of the present invention.

A spot size variability error can also contribute to a laser ablation profile error. FIG. 12A illustrates an RMS Distribution Graph, showing the fitting RMS error for several different refractive cases (refractive powers) at various spot sizes. FIG. 12B illustrates a PV Distribution Graph. The units on the x-axis represent the spot size diameter in millimeters. Based on the example shown in these figures, an optimal spot size (i.e. lowest error) for Flying Spot Scanning (FSS) can range from about 1.0 mm to about 1.6 mm, and more specifically can be about 1.5 mm or about 0.5 mm FWHM. The FWHM is often about one third of the spot size. In this way, an optimal spot size can be determined for each refractive case, which can confer the maximum inhibition of aberration in model optical surface shape. In this way, it is possible to control the amount of error by controlling the spot size.

A simple spherical refraction is shown in FIGS. 12A and 12B. The RMS and PV change may not be very significant over a big range (e.g. +3D to −6D), except possibly for the low refraction cases as shown in these examples. The optimal spot size may not appear to change with refractions, again except for very low refraction cases such as, for example, ±0.5D or cases close to emmetropia.

The VSS spot can range between 0.65 mm and 6.5 mm. Though only discrete number of spots are shown, it should be recognized that the spot sizes can be continuous. VSS can have an ablation depth of about 0.25 µm (tissue) while the FSS can have an optimal spot size of 1.5 mm with 0.5 mm FWHM and 0.4 µm depth Gaussian profile. Often, there is no variability of the FSS spot size, meaning that the spot size can be fixed. In some embodiments, the laser ablation profile variable includes a flying spot scanning factor ranging from about 1 mm to about 1.6 mm.

3. Grid Geometry

Figure 6:
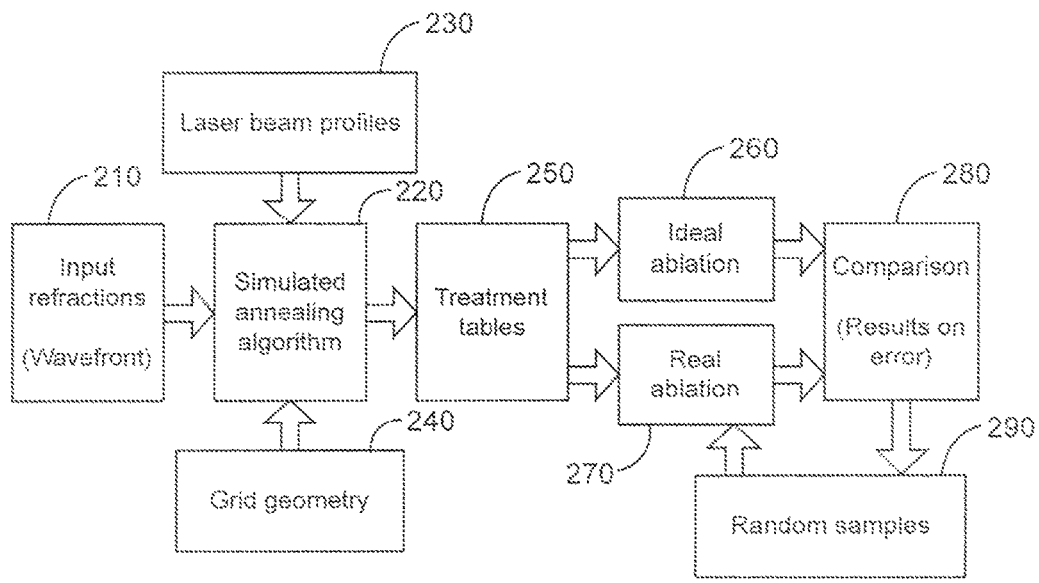
FIG. 6 illustrates a simulator flow diagram according to an embodiment of the present invention.

See FIG. 6, reference number 240. Grid geometry decides the solution space for the simulated annealing algorithm. In some embodiments, the wavefront device variable may include a 100 µm gridsize factor.

4. Ablation Algorithm

Figure 11A:
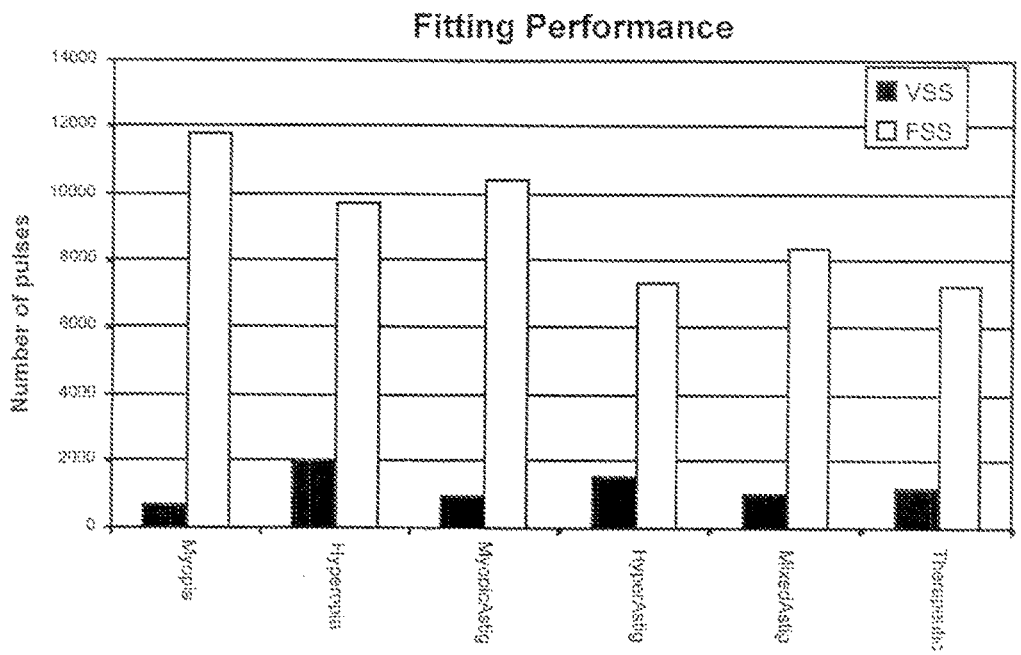
FIG. 11A illustrates fitting performance according to an embodiment of the present invention.

It is also possible to use fitting performance, which is related to the fitting error, to determine the number of ablation pulses employed to perform the ablation, as shown in FIG. 11A. In this example, the Flying Spot Scanning profile can have about 10,000 pulses, for example, for each of the refractive cases, whereas the Variable Spot Scanning profile can have less than about 1,000. Consequently, in this example if VSS operates at a laser pulse repetition rate of 20 Hz it takes about 50 seconds for the ablation. To perform an FSS ablation in the same amount of time, the system should operate at a laser pulse repetition rate of 200 Hz.

Figure 9C:
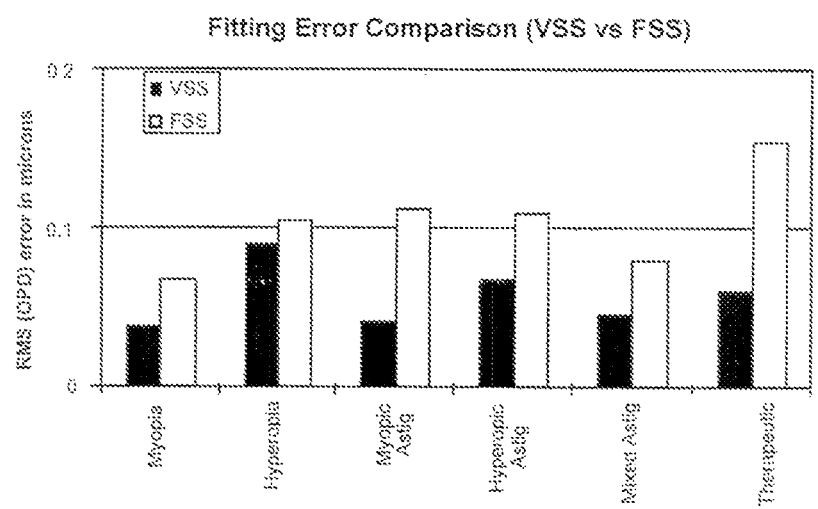
FIG. 9C illustrates a fitting error comparison according to an embodiment of the present invention.

An analysis of fitting error comparison of all 6 exemplary profile cases in shown in FIG. 9C, including fitting (algorithm), registration, tracking and beam uniformity. These 6 cases can be evaluated for RMS error with VSS and FSS being the two sets of beams. Laser pulse repetition rate for VSS is 10 Hz and FSS is 100 Hz. Based on FIG. 9C, it is clear that VSS is superior to FSS in all of the six refractive cases, based on the RMS error, with therapeutic and myopic astigmatism having the biggest gain, or difference between VSS and FSS.

Suitable ablation algorithm approaches are also discussed in U.S. Pat. No. 6,673,062, issued Jan. 6, 2004, the full disclosure of which is incorporated herein by reference.

C. Laser Registration and Tracking System Parameters

As shown in FIGS. 4 and 5, a laser registration and tracking system can include parameters corresponding to registration source errors ($\sigma_r^2$), and linear and torsional tracking source errors ($\sigma_t^2$). Accordingly, a laser registration and tracking system variable may be selected from the group consisting of a registration factor, a linear tracking factor, and a torsional tracking factor. In one embodiment, the laser registration and tracking system variable can include a registration accuracy less than about 10 µm in both the vertical and horizontal directions and a rotational error less than about 0.5°.

1. Registration Error

Registration error, position error, and rotational alignment error can be modeled or determined. The registration error is typically the sum of the position error and the rotational alignment error. In general, the pupil center at the time the wavefront is taken with an aberrometer or phoropter can differ from the pupil center at the time the treatment procedure is performed. This shift in pupil center position error can induce a high order aberration. Similarly, rotational alignment error can also contribute to an increase in high order aberrations. Further, pupil size changes and rotational or alignment errors can also contribute to aberrations. These aberrations can be modeled as randomly distributed errors.

Figure 13A:
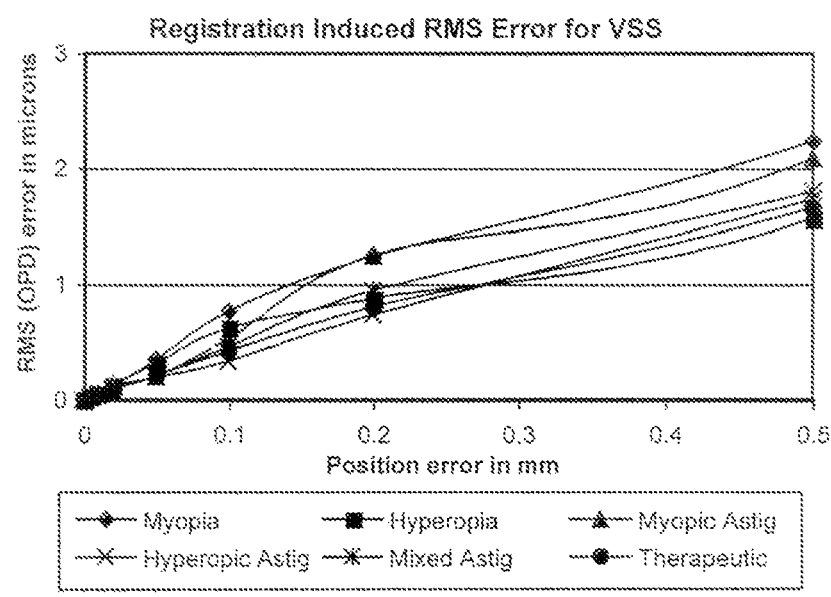
FIGS. 13A-E illustrate registration error analysis according to an embodiment of the present invention.
Figure 13B:
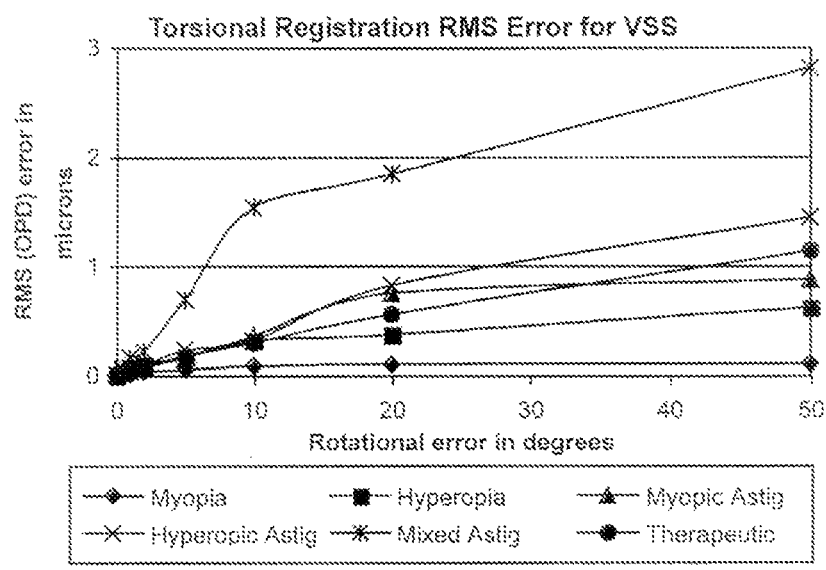
Figure 13C:
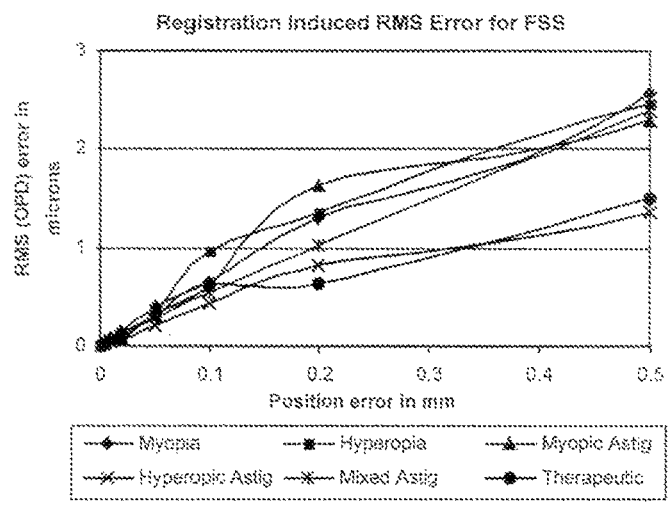
Figure 13D:
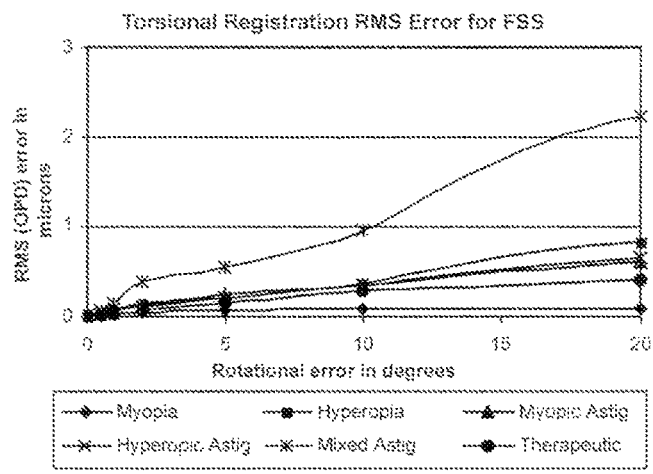
Figure 13E:
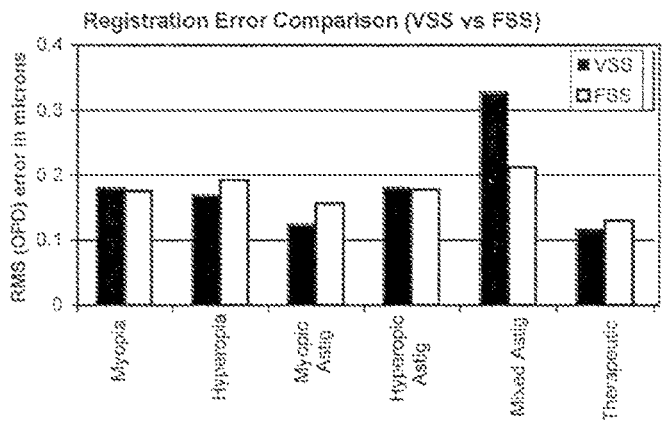

FIGS. 13A-E illustrate registration error analysis. For linear registration induced RMS error, VSS and FSS appear to perform similarly, as shown in FIGS. 13A and 13C, which depict linear, or X/Y, registration. VSS can be volumnable (larger) on mixed astigmatism. For the comparison, values of 20 µm accuracy in position and 5° in the rotational alignment can be used. In the case of a cylinder with a large angle, VSS registration can be larger than FSS registration, but theoretically, if there is no fitting error, they may be similar. FIGS. 13B and 13D depict VSS and FSS torsional registration induced RMS error, and based on these figures, torsional registration appears to be correlated to the refractive case. VSS and FSS torsional registration induced RMS error appear to behave similarly, and for mixed astigmatism, VSS appears to exhibit slightly more error which may be due to mixed astigmatism having the least symmetric profile. FIG. 13E shows a comparison between VSS and FSS for the combined linear and torsional registration error. Again, VSS and FSS combined linear and torsional registration induced RMS error appear to behave similarly, and for mixed astigmatism, VSS appears to exhibit slightly more error which may be due to mixed astigmatism having the least symmetric profile.

2. Linear and Torsional Tracking Errors

It may be desirable to keep the center of the pupil tracked during the whole course of ablation as the eye moves vertically, horizontally, and cyclo-rotationally. Thus, the tracking component can account for vertical, horizontal, and cyclo-torsional tracking. Parameters such as eye motion speed, duration of each motion, tracking speed, tracking accuracy, and the system latency time can be considered.

It can be helpful to evaluate eye motion during visual fixation. Without fixation, eye movement can be large. During fixation, the eye can undergo micro-motion, which can be modeled as a set of random walks with fixed speed and duration. This is often true for linear motion, although for torsional movement a similar approach can also be applied in terms of an error source parameter. In some cases, the linear motion can have a speed of about 5°-10°/second, or about 20 μm with duration of about 22 ms. Hence, a grid size of 1001×1001 can be used because the grid spacing will be 10 μm, which represents the distance between each location. The amount of torsional movement can be, for example, between 0.4°±0.3°.

Figure 14A:
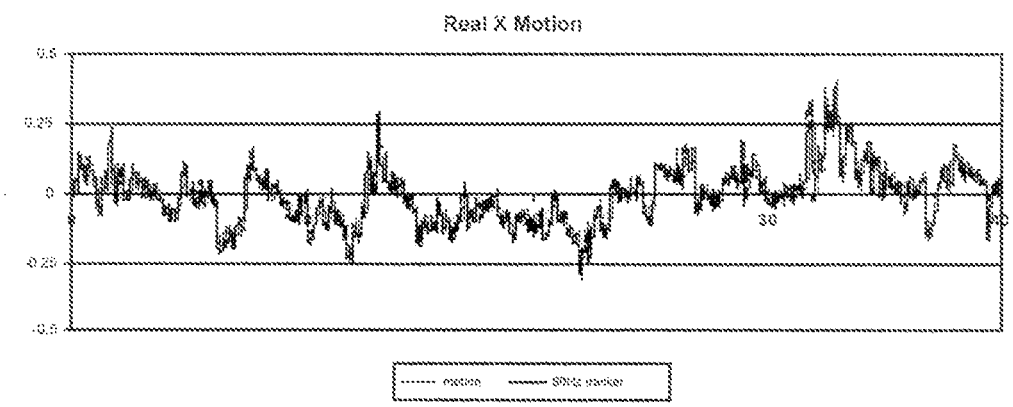
FIG. 14A illustrates real X motion according to an embodiment of the present invention.
Figure 14B:
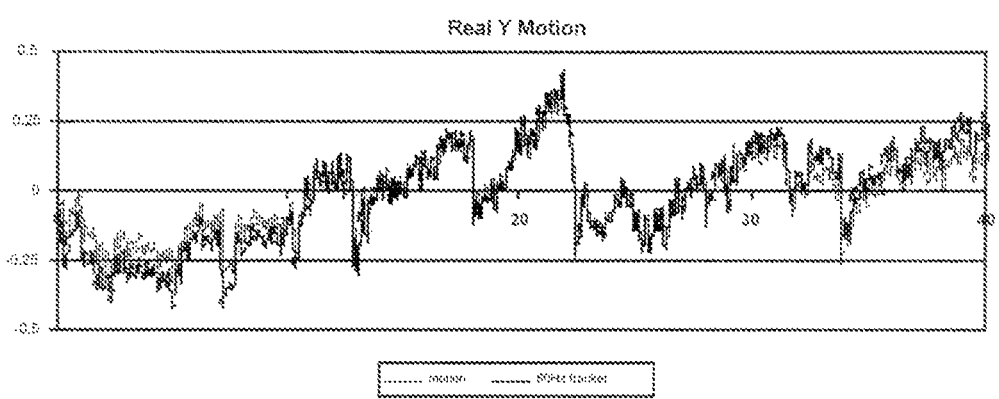
FIGS. 14B-D illustrate additional real and simulated eye motions according to an embodiment of the present invention.

45 real eye motions were captured with a 200 Hz eye motion camera and a 60 Hz VISX Eye Tracker. FIGS. 14A and 14B show the X and Y real motion of the 19th OS. For eye Y motion, the tracker can have tracking error ranging from about 0.5 mm to about 1.0 mm. Spectral analysis can provide another approach to eye motion analysis. In some embodiments, tracking can compensate for a certain amount of eye motion, and the uncompensated motion can contribute to a high order aberration.

Figure 14C:
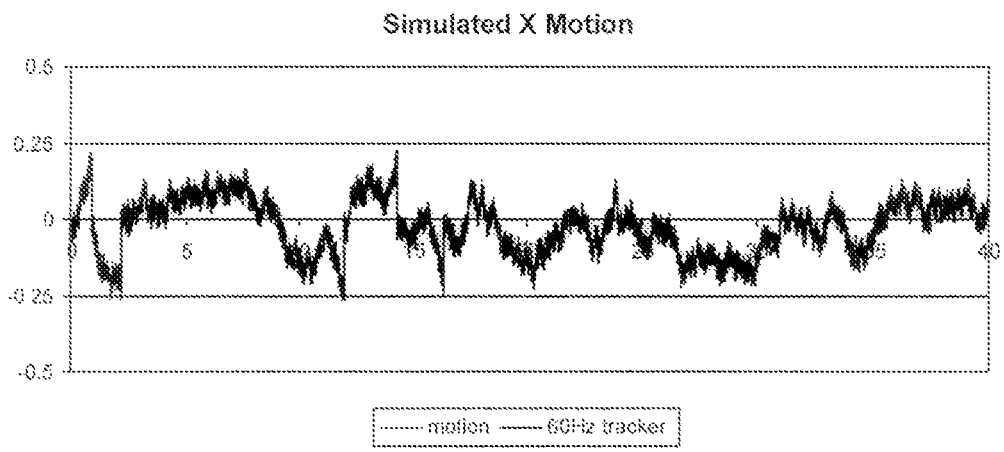
Figure 14D:
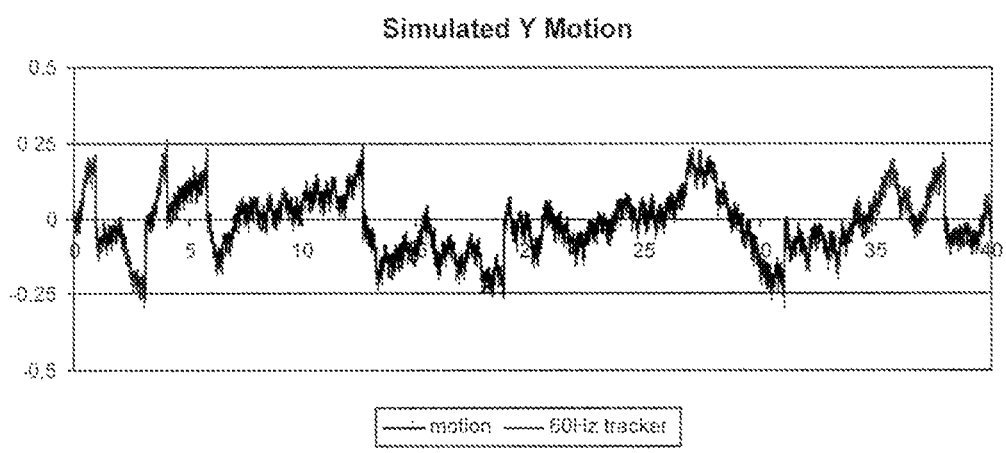

Types of eye movement include (a) saccadic motion, (b) smooth pursuit, (c) tremor, and (d) nystagmus. From the example shown in FIGS. 14A and 14B mostly smooth pursuit and saccadic motion is observed. The standard deviation can be about 0.1 mm. There are zones of deviation that are present toward the left and right side of the graphs, where the error is more easily observed. FIGS. 14C and 14D show simulated eye movement examples that are comparable to real eye movement shown in FIGS. 14A and 14B.

FIGS. 15A-15F illustrate a comparison of VSS and FSS observed tracking efficiency. Tracking efficiency can be based on tracking speed, tracking accuracy, and system latency time. A model for eye tracking in the X-Y (or vertical/horizontal) direction can be constructed, based on the following input parameters:

| parameter | description |
|---|---|
| num | number of treatment |
| gridsize | grid size for wavefront |
| speed | eye movement (mm/s) |
| duration | eye movement time (s) |
| laser pulse repetition rate | 10 Hz VSS |
| | 100 Hz FSS |
| tracking rate | tracking speed (Hz) |
| tracking error | accuracy (mm) |
| system latency time | how fast system responds (s) |

Figure 15A:
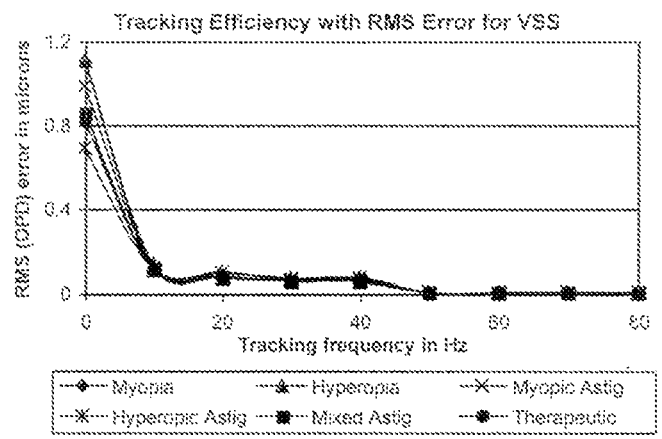
FIGS. 15A-F illustrate a comparison of VSS and FSS observed tracking according to an embodiment of the present invention.
Figure 15B:
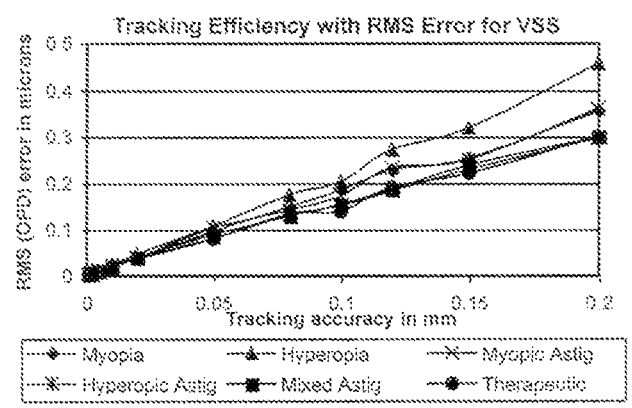
Figure 15C:
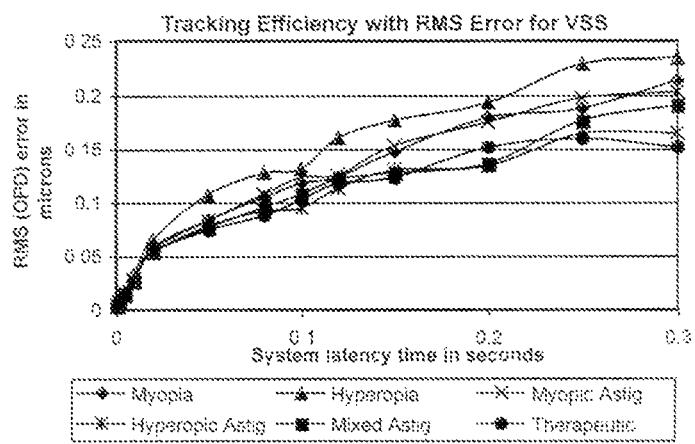
Figure 15D:
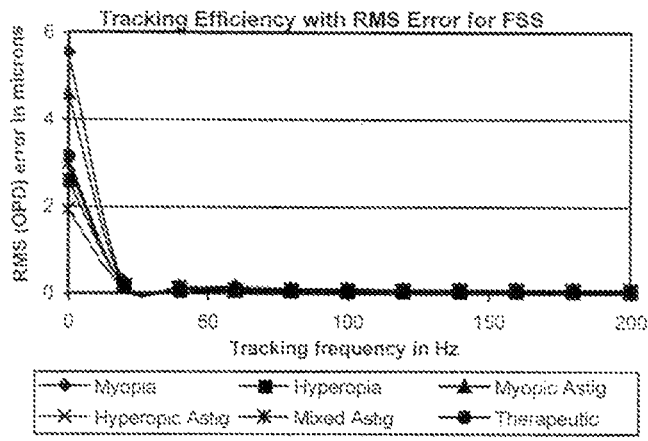
Figure 15E:
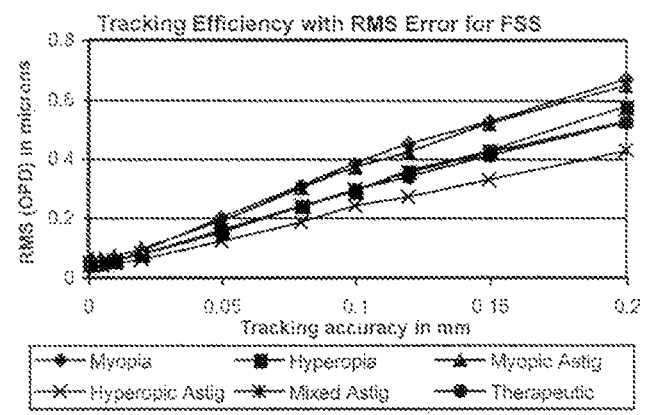
Figure 15F:
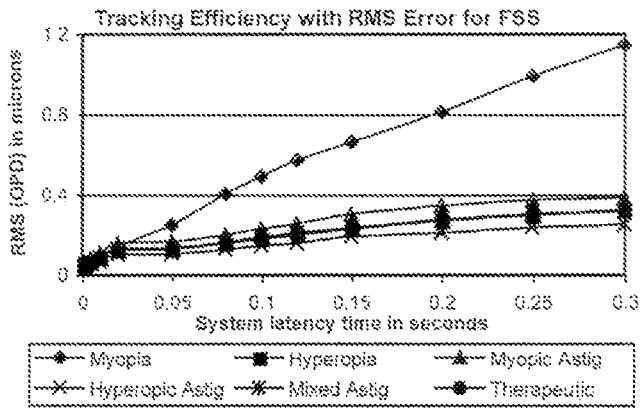
Figure 16A:
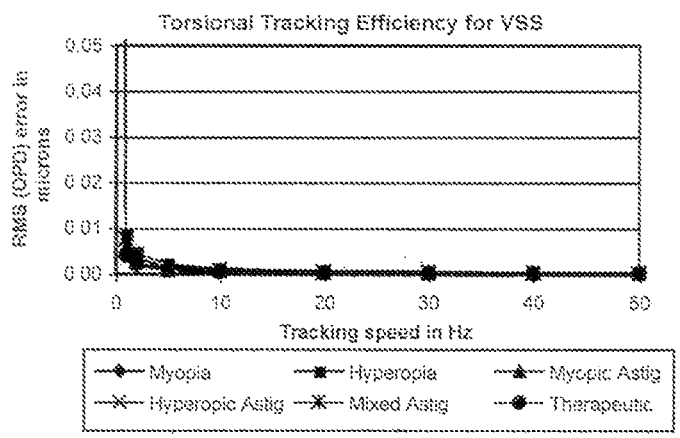
FIG. 16A illustrates VSS torsional tracking efficiency according to an embodiment of the present invention.
Figure 16B:
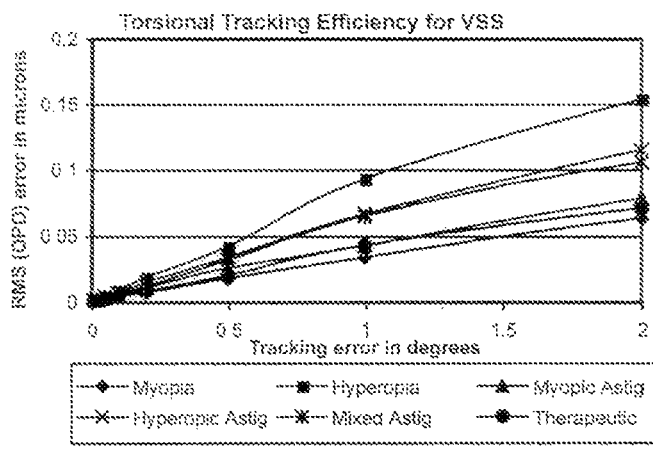
FIG. 16B illustrates torsional tracking efficiency with RMS error for VSS, with respect to tracking error, according to an embodiment of the present invention.
Figure 16C:
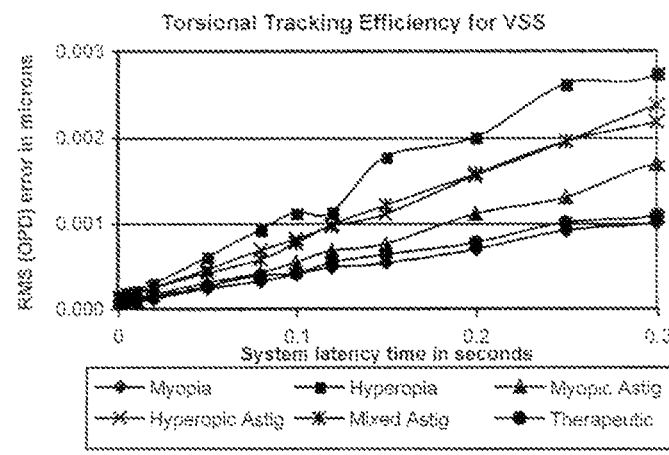
FIG. 16C illustrates torsional tracking efficiency with RMS error for VSS, with respect to system latency, according to an embodiment of the present invention.
Figure 16D:
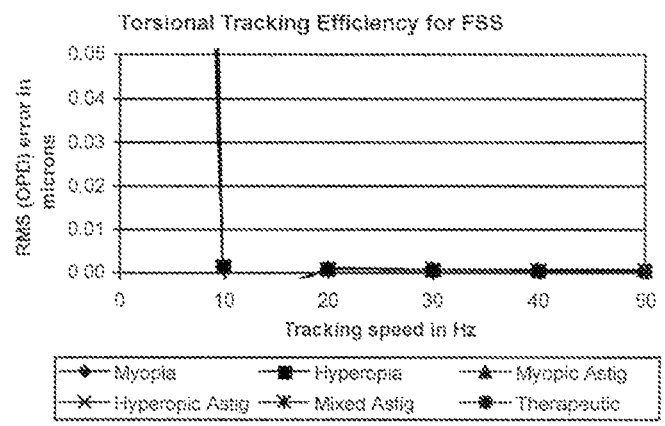
FIG. 16D illustrates torsional tracking efficiency for FSS, with respect to tracking speed, according to an embodiment of the present invention.
Figure 16E:
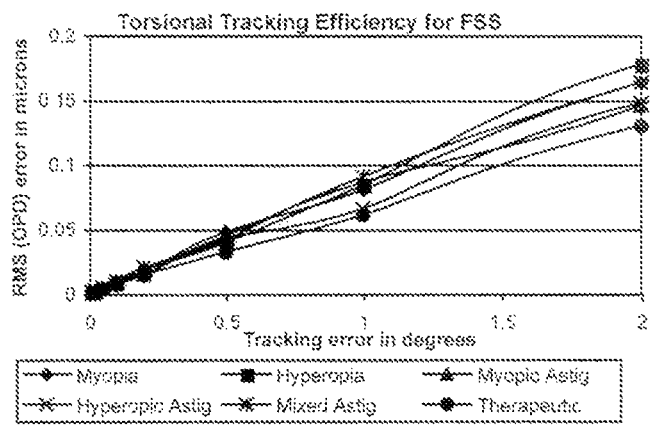
FIG. 16E illustrates torsional tracking efficiency for FSS, with respect to tracking error, according to an embodiment of the present invention.
Figure 16F:
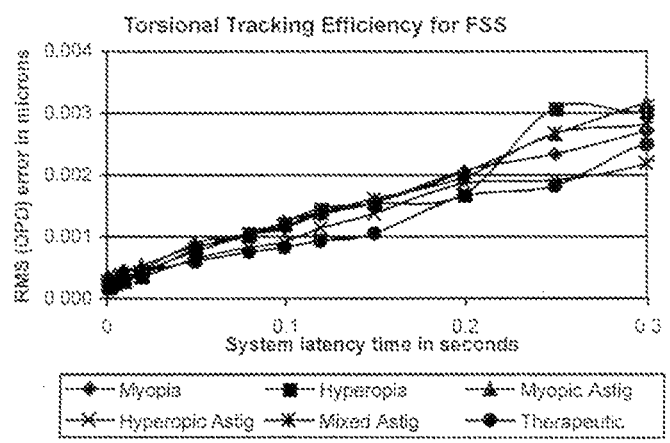
FIG. 16F illustrates torsional tracking efficiency for FSS, with respect to system latency, according to an embodiment of the present invention.

In one example, a 2 mm/s eye speed and 0.022 s duration were used. According to the results, the tracking speed can be exponential (FIGS. 15A and 15D), the tracking error can be linear (FIGS. 15B and 15E), and the latency time can be quadratic (FIGS. 15C and 15F). In FIGS. 15A and 15D, no tracking accuracy and system latency errors were assumed. In FIGS. 15B and 15E, no tracking speed and system latency errors were assumed. In FIGS. 15C and 15F, no tracking speed and tracking accuracy errors were assumed.

FIGS. 16A-16F show a comparison of torsional tracking efficiency between VSS and FSS. Based on this data, torsional tracking error values appear to be lower than horizontal and vertical tracking error values. Overall, the linear tracking appears to be one magnitude larger than torsional tracking error. However, when the torsional tracker is not on, the error is larger, especially for FSS. In general, the tracker error is about twice as large for FSS, as compared to VSS.

Figure 17A:
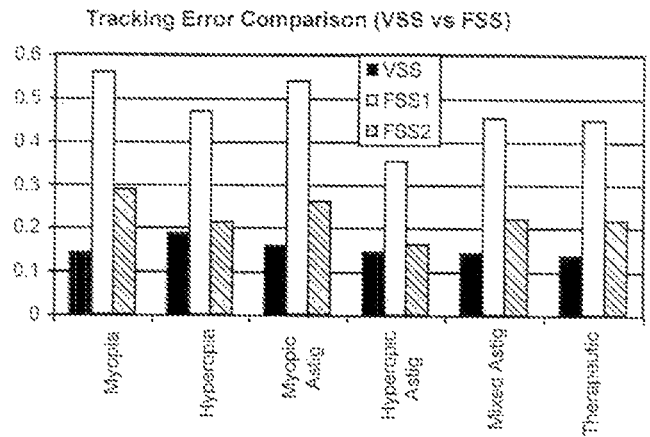
FIG. 17A illustrates a tracking error comparison between VSS and FSS according to an embodiment of the present invention.
Figure 17B:
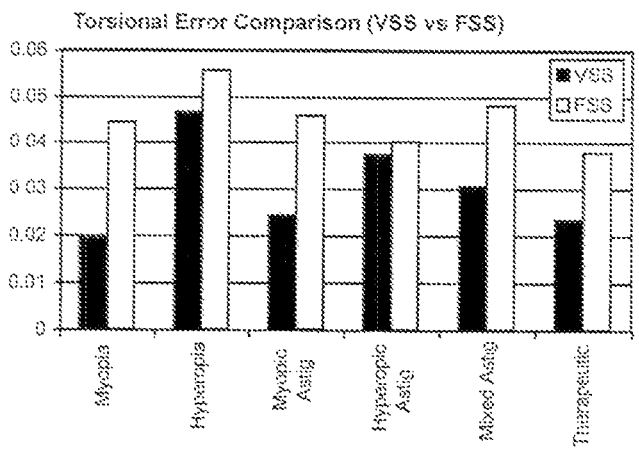
FIG. 17B illustrates a torsional error comparison between VSS and FSS according to an embodiment of the present invention.
Figure 17C:
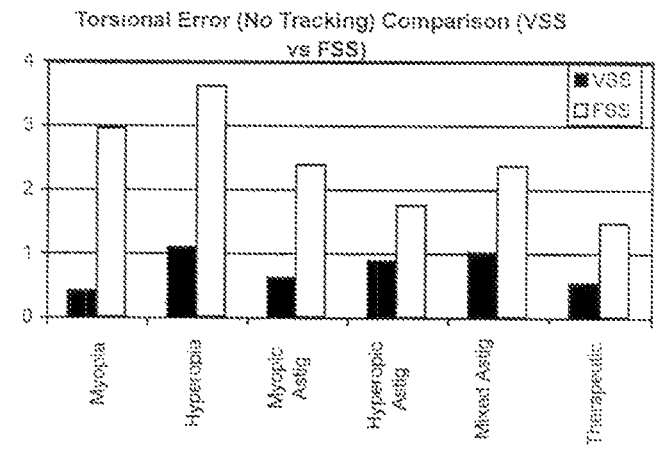
FIG. 17C illustrates a torsional error (no tracking) comparison between VSS and FSS according to an embodiment of the present invention.

FIGS. 17A-C show linear and torsional tracking error comparisons between VSS and FSS. For linear tracking, 60 Hz tracking for FSS1, VSS as well as for torsional was used, and 120 Hz was used for FSS2. This example also used 2 mm/s with 0.022 ms duration for linear eye movement, 0.1°/s with 5 s duration for torsional movement. Linear 0.05 mm accuracy and 0.1 s latency time, torsion 0.5° accuracy and 0.1 s latency time values were observed. Based on these figures, it appears that VSS confers lower errors than FSS.

In one embodiment, the laser ablation profile variable includes a variable spot scanning factor, and the laser registration and tracking system variable includes a tracking accuracy less than about 20 μm in both the vertical and horizontal directions, a latency time less than about 10 ms, and a tracking speed of about 60 Hz or greater. In another embodiment, the laser ablation profile variable includes a flying spot scanning factor, and the laser registration and tracking system variable includes a tracking accuracy less than about 5 μm in both the vertical and horizontal directions, a latency time less than 5 ms, and a tracking speed of about 200 Hz or greater. Relatedly, the laser ablation profile variable can include a variable spot scanning factor, and the laser registration and tracking system variable can include a cyclo-torsional tracking angular accuracy of about 0.5° or better. Likewise, the laser ablation profile variable can include a flying spot scanning factor, and the laser registration and tracking system variable can include a cyclo-torsional tracking angular accuracy of about 0.25° or better.

In other embodiments, the laser ablation profile variable includes a variable spot scanning factor, and the laser registration and tracking system variable includes a laser energy fluctuation less than about 4%. Similarly, the laser ablation profile variable can include a flying spot scanning factor, and the laser registration and tracking system variable can include a laser energy fluctuation less than about 2%.

D. Laser Delivery System Parameters

As noted above, a laser ablation profile variable can be selected from the group consisting of a pulse size factor, a spot size variability factor, a beam uniformity factor, and a laser pulse repetition rate factor.

1. Beam Uniformity and Variability

Laser beam uniformity source errors can be represented as $\sigma_b^2$, and can result from the laser beam profile deviating from the theoretically claimed shapes due to micro-fluctuations in the energy profile. It is also possible that the laser energy fluctuates over time due to physical or mechanical reasons producing laser beam variability.

For laser beam uniformity, the laser energy can be fluctuating during ablation. This energy fluctuation can cause deviation of ablation depth in each laser pulse. This deviation can eventually translate to high order RMS errors. Typically, laser beam uniformity is not dependent on the laser pulse repetition rate.

Figure 18A:
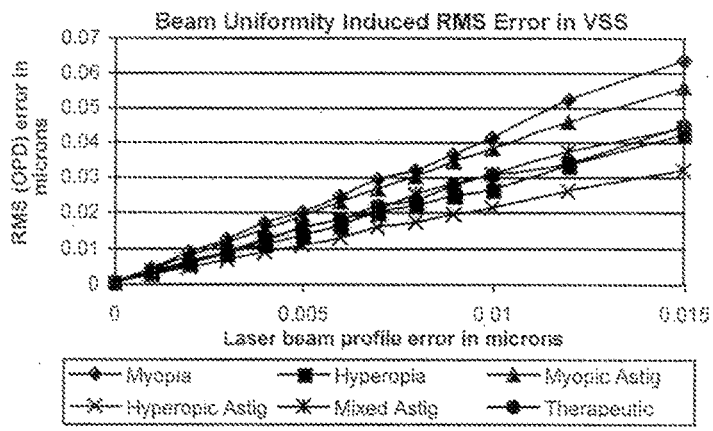
FIG. 18A illustrates a beam uniformity induced RMS error in VSS according to an embodiment of the present invention.
Figure 18B:
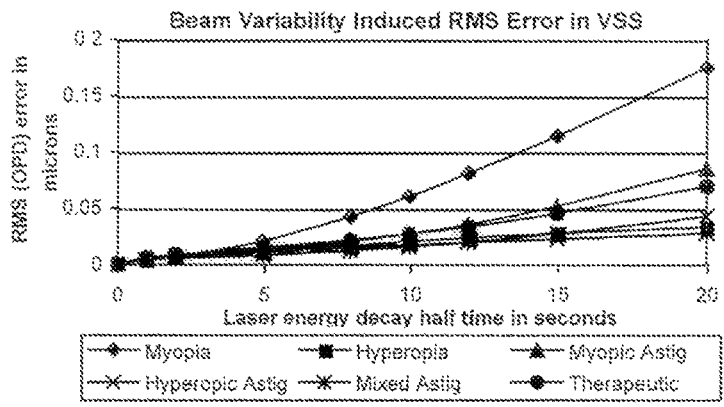
FIG. 18B illustrates a beam variability induced RMS error in VSS, with respect to laser energy decay, according to an embodiment of the present invention.
Figure 18C:
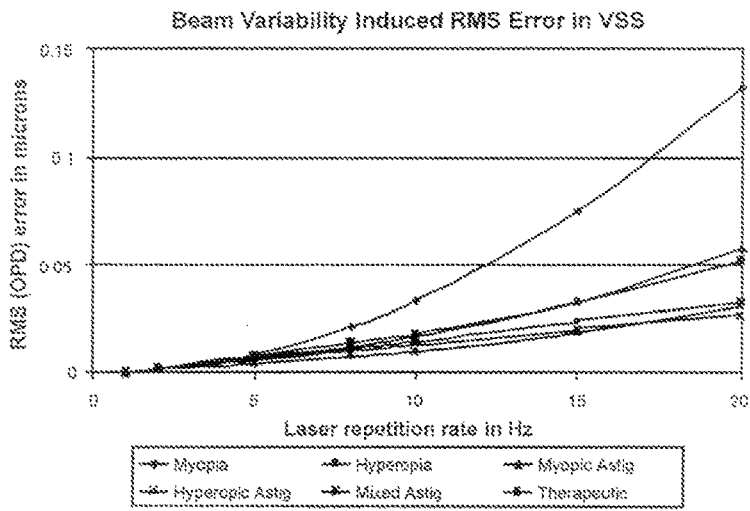
FIG. 18C illustrates a beam variability induced RMS error in VSS, with respect to laser pulse repetition rate, according to an embodiment of the present invention.
Figure 18D:
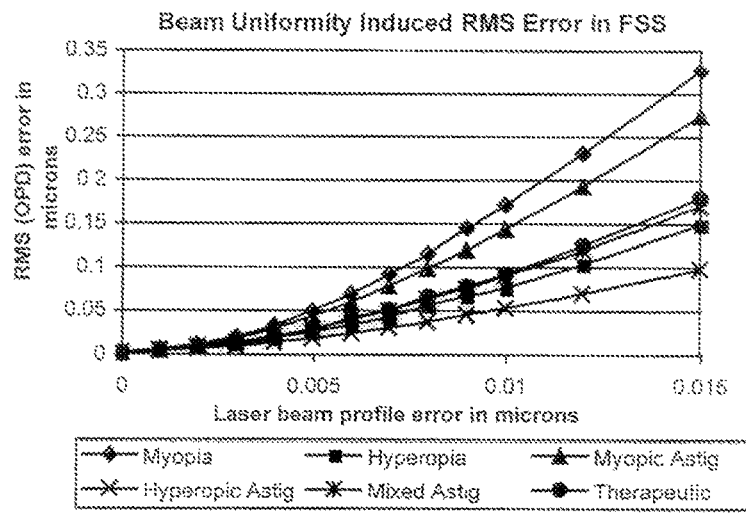
FIG. 18D illustrates a beam uniformity induced RMS error in FSS according to an embodiment of the present invention.
Figure 18E:
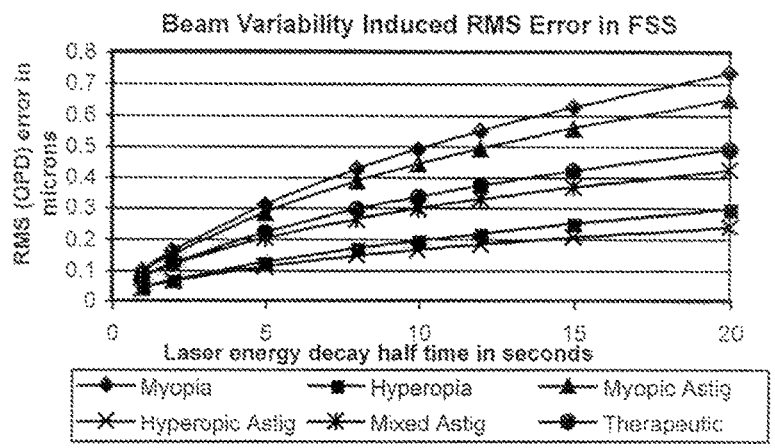
FIG. 18E illustrates a beam variability induced RMS error in FSS, with respect to laser energy decay, according to an embodiment of the present invention.
Figure 18F:
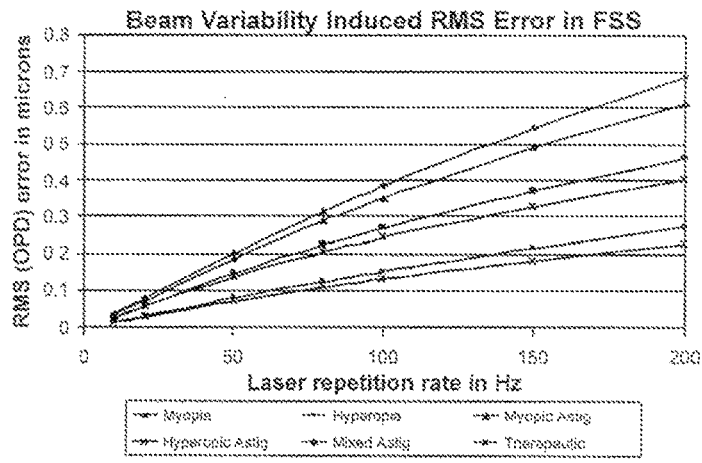
FIG. 18F illustrates a beam variability induced RMS error in FSS, with respect to laser pulse repetition rate, according to an embodiment of the present invention.

FIGS. 18A and 18D show laser beam uniformity analysis, and FIGS. 18B, 18C, 18E, and 18F show laser beam variability analysis. Micro-fluctuations and variability may be due to laser energy decay because of ozone formation. FIG. 18A considers uniformity only, without decay. Often, the first 20 seconds the laser is pulsed are considered when determining whether high order aberrations are induced. Exponential time decay (half time) can be about 7 seconds. Two factors to consider are decay half time and laser pulse repetition rate. Laser beam variability may be dependent on laser pulse repetition rate.

Figure 19A:
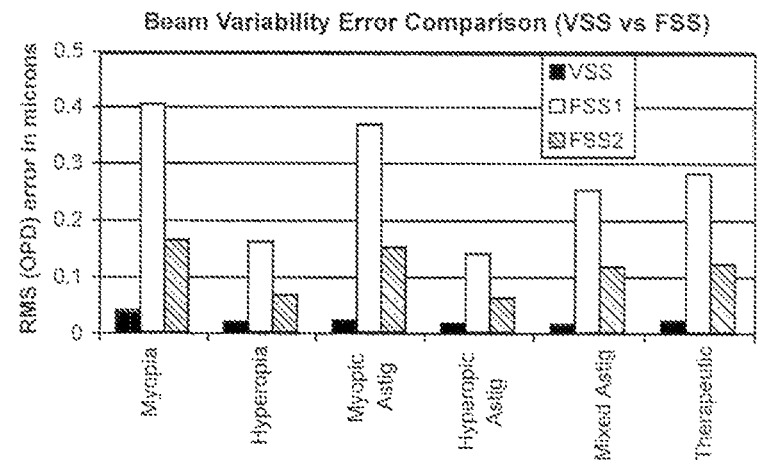
FIG. 19A illustrates a beam variability error comparison between VSS and FSS according to an embodiment of the present invention.
Figure 19B:
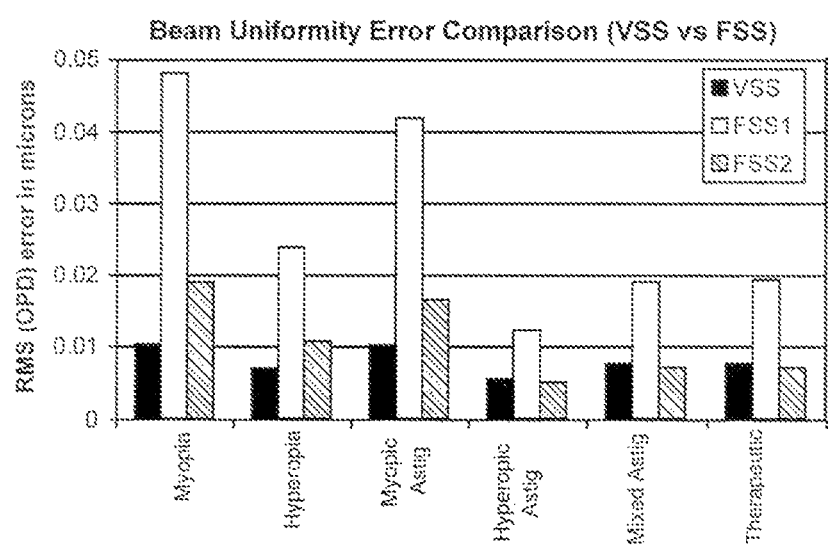
FIG. 19B illustrates a beam uniformity error comparison between VSS and FSS according to an embodiment of the present invention.

FIGS. 19A and 19B are derived from known uniformity and variability calculations. Such analysis can include factors such as ozone buildup, laser decay, and uniformity change, which can cause or amplify high order aberrations and/or under-correction. For the VSS case, a 7 second decay half time is assumed, as is the case for FSS1. For FSS2 the decay half time is 2 seconds. For uniformity, ±1% error in laser energy is assumed for VSS. Apparently, the error induced by laser energy micro-fluctuation is much smaller. For uniformity for FSS, FSS1 used ±1% error in laser energy while FSS 2 used ±0.5% error. Laser beam uniformity and variability are further discussed in U.S. patent application No. 60/553,580, filed Mar. 15, 2004, the full disclosure of which is incorporated herein by reference.

2. Laser Pulse Repetition Rate

Another laser ablation profile variable is the laser pulse repetition rate factor. In some VSS embodiments, the laser pulse repetition rate can range from 10 Hz to about 20 Hz. In some FSS embodiments, the laser pulse repetition rate can range from about 100 Hz to about 200 Hz.

E. Microkeratome Parameters

Microkeratome source errors can be represented as $\sigma_m^2$, and can result from aberrations associated with, for example, a LASIK flap. The LASIK flap is typically generated from a LASIK procedures, but not PRK or LASEK. The LASIK flap may tend to induce spherical aberrations and coma, and the orientation of the coma may be consistent with the orientation of the LASIK flap hinge. Microkeratome-induced errors, represented by Zernike polynomials, may spread to all modes. The general consideration lies on the biomechanical changes of the stroma both long term and short term. The water content redistribution and stress changes in different layers of lamella cause deformation of the cornea.

Biomechanical effects of microkeratome incision were described in more detail by Cynthia Roberts ("The cornea is not a piece of plastic", *J. Refract. Surg.* 16(4): 407-413 (2000), while aberration effects were studied by Jason Porter et al. ("Separate effects of the microkeratome incision and laser ablation on the eye's wave aberration", *Am. J. Ophthalmol.* 136(2): 327-337 (2003), the full disclosures of which are incorporated herein by reference.

It is possible to take an approach that only considers a population average effect on the induced spherical aberrations as well as coma. It is possible to claim, on average, 0.1 micron in spherical aberration and a 0.1 microns in coma (at the same orientation as flap hinge). Therefore, the combined effect, represented as a lasik flap error, can often be at the order of 0.15 microns. Microkeratome parameters may include spherical aberrations (e.g. central flattening and peripheral thickening effects), hinge effects, and orientation effects. A LASIK flap box may also reflect a biomechanical effect that it based on a laser/tissue interaction.

1. Spherical Aberration

After a flap cut, there may be a central flattening and a peripheral thickening of the cornea, hence inducing positive spherical aberrations. In some embodiments, the microkeratome variable can include an induced positive spherical aberration between about 0.1 microns and about 0.3 microns. In some embodiments, the microkeratome variable can include a coma in the direction of the microkeratome hinge in an amount between 0.1 microns and 0.3 microns.

2. Hinge Effect

However, due to the hinge of the flap, the spherical aberration induced might not be circularly symmetric. Therefore, a small amount of coma can also be induced.

3. Orientation Effect

It is possible to model the flap effect as a random process to induce positive spherical aberration as well as direction oriented (toward hinge direction) coma as $$\sigma_m^2 = \sigma_{sph}^2 + \sigma_{coma}^2, \quad (10)$$

where $\sigma_m^2$ represents the total error of the flap effect, $\sigma_{sph}^2$ represents the error induced by the positive spherical aberration, and $\sigma_{coma}^2$ represents error induced by the coma.

F. Healing Effect

Finally, the healing effect is a smoothing process, which can be modeled as a Gaussian kernel applied to the final wavefront. In general, this is an error reduction process for random noise but an error generation process for uniform error-free shapes. It is possible that the smoothing effect of healing can reduce a local RMS error while not reducing the overall RMS error. The healing effect can be expressed as H(•) The healing effect can be considered as a low pass filter. The healing effect can be thought of as a first order Butterworth low-pass filter. It may be desirable to simplify the model to be a standard Gaussian filter. There are two reasons for doing that. First, the first order Butterworth filter can be approximated with a standard Gaussian filter. Second, the Gaussian filter is often more commonly used, and may be easier to implement than Butterworth. See David Huang et al. ("Mathematical model of corneal surface smoothing after laser refractive surgery", *Am. J. Ophthalmol.* 135(3): 267-278 (2003), which is incorporated herein by reference.

In some embodiments, the healing effect variable includes a Gaussian kernel with 2 micron in height and 0.5 mm in full width at half maximum (FWHM).

Figure 20:
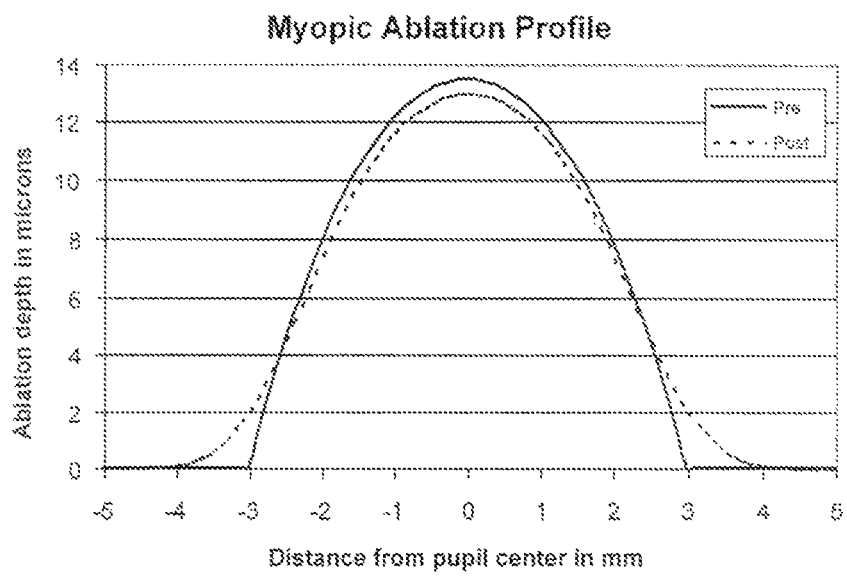
FIG. 20 illustrates an input myopic ablation profile pre- and post-healing according to an embodiment of the present invention.
Figure 21:
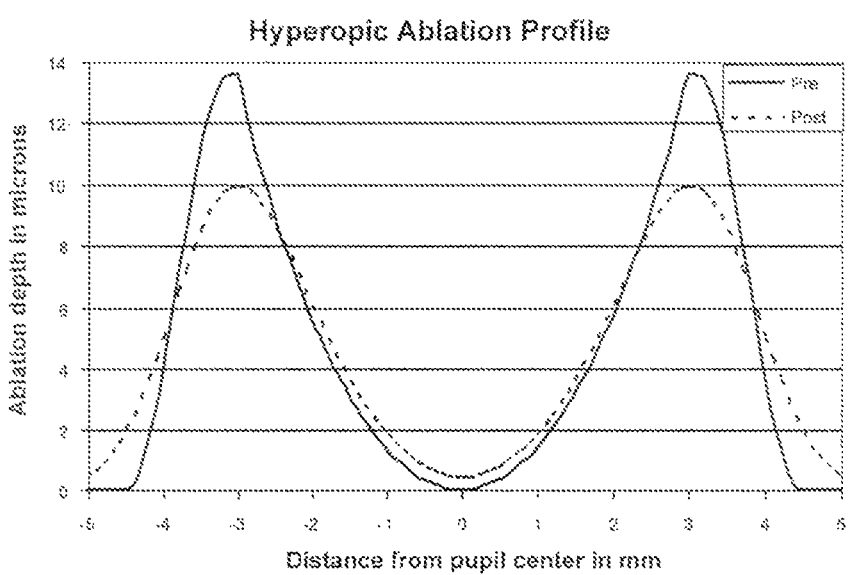
FIG. 21 illustrates an input hyperopic profile pre- and post-healing according to an embodiment of the present invention.

FIG. 20 shows the healing effect with a Gaussian filter for a −1D myopic treatment profile (Munnerlyn shape) with a 6 mm pupil. FIG. 21 shows the healing effect with a Gaussian filter for a +1D hyperopic treatment profile (Munnerlyn shape) with a 6 mm pupil. In both cases the resulting healing effect compared very well with those shown in Huang et al. (see above).

With the application of a Gaussian filter, the end effect is that it may alter the general, or ideal, shape to induce some low order aberrations as well as some lower high order aberrations such as coma and spherical aberrations. However, at the same time, it can also smooth out some higher order aberrations due to its nature of smoothing out rapid fluctuations.

Figure 22:
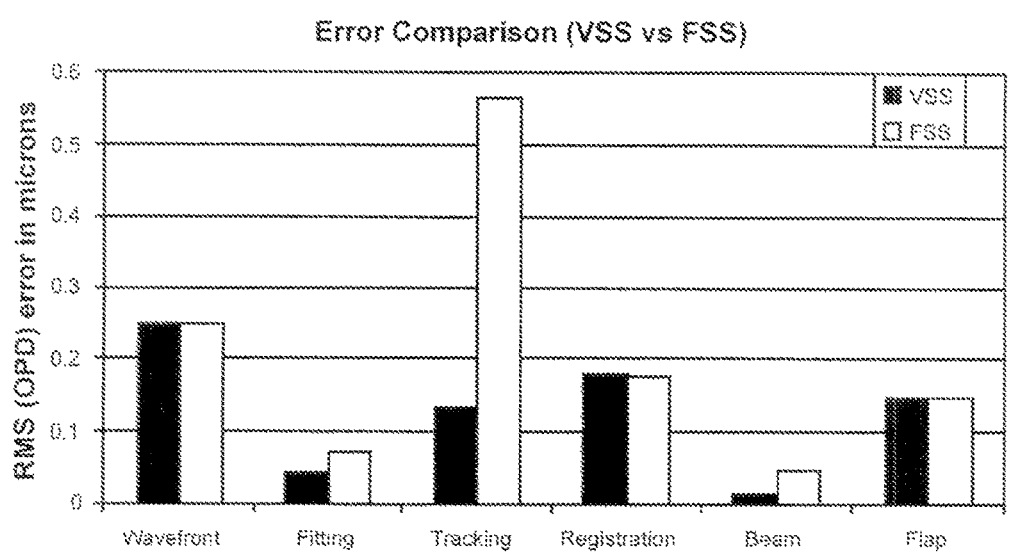
FIG. 22 illustrates an error comparison between VSS and FSS, without a healing effect.

FIG. 22 illustrates the error from different error sources without consideration of healing effect. Apparently, registration, tracking, wavefront device error and flap effect may be somewhat more important than the laser beam variability as well as fitting error. The error due to healing may reduce the high order RMS errors because it has a "smoothing" effect. It may also induce additional somewhat lower order and some lower high order aberrations such as sphere, cylinder, comas and spherical aberrations. It is possible to consider healing as one of the factors that affects the overall refractive surgery outcome.

III. Determining a Model Optical Surface Shape Based on the Target Optical Surface Shape and a Set of Refractive Surgery System Parameters Given a target optical surface shape (e.g. refractive case) and a set of refractive surgery system parameters, it is possible to determine or predict a model optical surface shape. Essentially, this is the target optical surface shape "as applied" by the surgery system, and can also represent an optical surface shape after healing. In one embodiment, the present invention provides a system for inhibiting an induced aberration resulting from refractive surgery, where the system includes an input that accepts a target optical surface shape; a module that determines a model optical surface shape based on the target optical surface shape and a set of refractive surgery system parameters; and a module that adjusts the set of refractive surgery system parameters so as to inhibit an aberration in the model optical surface shape.

IV. Comparing the Target Optical Surface Shape and the Model Optical Surface Shape to Determine an Aberration Distribution The comparison of the target optical surface shape and the model optical surface shape can be based on a metric selected from the group consisting of an accuracy variable, a heating variable, and a treatment time variable. The accuracy variable can be based on a root mean squares error factor. The heating variable can be based on a temperature factor. The treatment time variable can be based on an ablation time factor.

V. Adjusting the Set of Refractive Surgery System Parameters so as to Inhibit the Aberration The adjustment of the set of refractive surgery system parameters can be based on a metric selected from the group consisting of an accuracy variable, a heating variable, and a treatment time variable. The accuracy variable can be based on a root mean squares error factor. The heating variable can be based on a temperature factor. The treatment time variable can be based on an ablation time factor.

VI. Simulation

The present invention provides an approach to modeling components of a refractive correction system. Any of the system parameters discussed above that can introduce errors or contribute to or exacerbate aberrations can also be simulated. Because system parameter error sources can contribute to or amplify aberrations in a model optical surface shape, adjustment of system parameters such as the accuracy of registration, the accuracy of fitting in the ablation algorithm, the tracker speed, the accuracy and system latency time of tracking, the laser beam uniformity and variability, or any other system component, can have effects on those aberrations.

Simulated laser systems can be useful in modeling the effects of various system components, and the present invention provides laser simulators for simulating laser ablation. An exemplary flow diagram of a laser refractive surgery system simulator is shown in FIG. 6. The simulator includes an input refraction module 210, a laser beam profile module 230, a grid geometry module 240, a simulated annealing algorithm module 220, a treatment table module 250, an ideal ablation module 260, a real ablation module 270, a comparison module, 280, and a random sample module 290.

A. Input Refractions

A simulator may include an input refraction module 210 that can present various target optical surface shapes, or refractive cases, to the simulator. Such target optical surface shapes may include low order refractive cases such as myopic, hyperopic, myopic astigmatism, hyperopic astigmatism, and mixed astigmatism, and may also include high order refractive cases such as a therapeutic case from a real eye that has more than 1.0 microns high order total RMS error. Often refractive cases are determined from a wavefront measurement device.

B. Laser Beam Profiles

A simulator may include a laser beam profile module 230. In simulating fitting errors for, example, a laser beam profile 230, a 100 micron grid size can be used. A validator, which can simulate the laser ablation, and a pulse instruction, which can simulate the characteristic of each laser pulse, can be used to formulate the basis data for different cases, such as VSS and FSS.

For a 100 µm sampling resolution in the algorithm fitting of the surface to be solved, flying Gaussian small spot scanning with spot size of or around 1.5 mm (FWHM 0.5 mm (FSS)) was observed to give a smaller amount of RMS errors compared to other spot sizes.

A laser simulator can be constructed such that given a set of commands (e.g. beam size and location) the accumulated tissue surface during the ablation can be modeled. The basis laser beam shapes, or the craters created by each individual pulse can be, for example, the flat top shapes for the variable spot scanning (VSS) or a Gaussian shape with 0.5 mm FWHM for the flying spot scanning (FSS). A laser registration and tracking component, as well as a laser delivery component, can be incorporated into the real ablation module 270.

For the fitting error, the input shape can be based on a wavefront surface. This shape is given to the fitting algorithm for the ideal ablation solution. A calculated list of commands (e.g. spot size and position), when passed through the laser simulator, can form another surface, the real ablation solution. The difference in the two surfaces can be represented as an RMS error. In general, it is possible to obtain a more accurate result if the spot size is smaller. However, due to the limitation in grid size, smaller spot size may not result in smaller fitting error. In addition, if the spot size can be variable, the fitting error can also be smaller.

C. Grid Geometry

A simulator may include a grid geometry module 240. As discussed above, it is helpful to use at least 1001×1001 grid size, that is, 10 µm resolution for the simulation. But the program can be designed with any configuration for grid size or grid geometry.

D. Simulated Annealing Algorithm

A simulator may include a simulated annealing algorithm module 220. The example wavefronts are then used for the algorithm module 220 to determine an ablation solution. Algorithm module 220 here is analogous to the algorithm box of FIG. 4. Laser beam profiles 230 can provide basis data for constructing laser delivery beam profiles to drive a simulated annealing algorithm, and grid geometry 240 can determine the solution space for the simulated annealing algorithm.

E. Treatment Tables

A simulator may include a treatment table module 250. It is possible to calculate the treatment table 250 with a simulated annealing algorithm for both VSS and FSS. The same treatment table 250 can be used to adjust variation on the specific basis data for any pulse profile (e.g. VSS or FSS) to determine both the ideal ablation 260 and the real ablation 270. Thus, VSS can be associated with a real ablation and an ideal ablation, and similarly FSS can be associated with a real ablation and an ideal ablation. For each case (e.g. VSS, ideal ablation), there can be 6 input shapes (e.g. myopia, hyperopia, myopic astigmatism, hyperopic astigmatism, mixed astigmatism, and a high-order based therapeutic case). A fitting error can be included prior to table creation. Typically, the treatment table is not considered to contain significant errors. However, a simulated annealing algorithm may introduce certain errors.

In the instance where the treatment table 250 is used to determine the ideal ablation 260, no device errors are assumed, and essentially the target optical surface shape becomes the ideal ablation. In the instance where the treatment table 250 is used to determine the real ablation 270, certain device errors are assumed, and essentially the target optical surface shape is used to determine the model optical surface shape.

For tracking in vertical and horizontal directions, the limitation can be set to 20 µm tracking accuracy and system can respond quicker than 10 ms, and tracking speed of 60 Hz for VSS. In the case of FSS, the vertical and horizontal tracking accuracy should be less than 5 μm and the system latency time shorter than 5 ms with a 200 Hz tracking speed.

For cyclo-torsional tracking, the angular accuracy can be within half a degree for VSS and within a quarter degree for FSS. As for laser beam uniformity and variability, VSS benefits from laser energy fluctuation less than 4% and FSS benefits from fluctuation less than 2%.

Figure 23A:
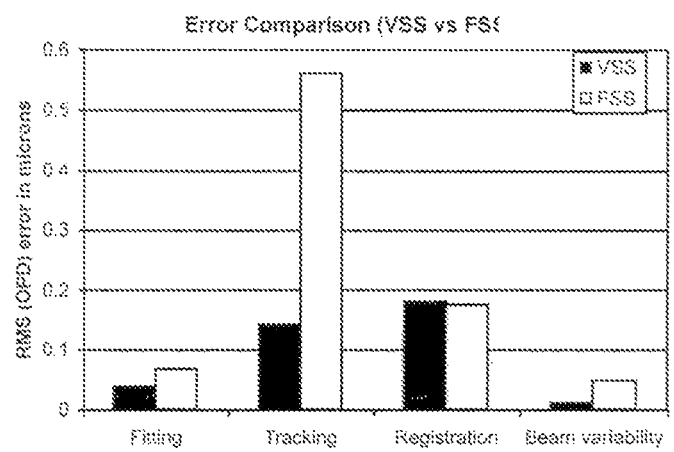
FIGS. 23A and 23B illustrate comparisons of VSS and FSS for various error sources according to an embodiment of the present invention.
Figure 23B:
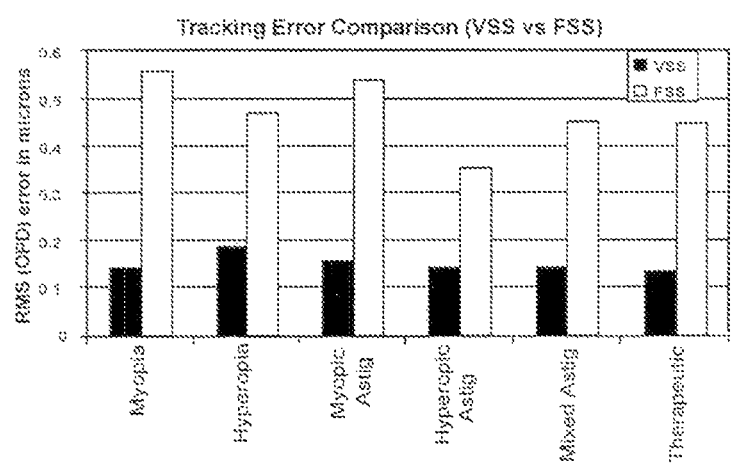

Of the various error sources, tracking error and registration error appear to be relatively large, as can be seen from FIGS. 23A and 23B, which show a comparison of VSS and FSS for various error sources for a myopia case (FIG. 23A) and for tracking error only for all refractive cases (FIG. 23B). In general, VSS performs better than FSS in terms of fitting, tracking, and beam variability. In order to correct high order aberrations, limitations on each component in a refractive surgery system can be considered in the system design phase. To achieve same-level error reduction, FSS systems may benefit from tighter restrictions.

For tracking errors, 60 Hz tracking speed, 0.05 mm tracking accuracy, and 0.1 s system latency time can be assumed. As for registration, 0.025 mm and 2° alignment error can be used. Finally, in beam variability simulation, a 1% fluctuation in delivered laser energy can be assumed. Different parameters with all six refractive cases can be applied to all simulations.

Cyclo-torsional registration was observed to induce only about one tenth RMS error as compared to registration in vertical and horizontal position errors. Cyclo-torsional tracking was observed to induce only about one tenth RMS error as compared to tracking in vertical and horizontal eye movements.

Simulations of tracking can be based on studies of eye motion. Parameters such as eye motion speed, duration of each motion, tracking speed, tracking accuracy, and the system latency time can be used in the simulation.

F. Ideal Ablation

A simulator may include an ideal ablation module 260. Typically, the ideal ablation will contain no errors. When applied with no device errors, the overall induced root-mean-squares (RMS) error should be zero. Ideal shapes can be useful, for example, in evaluating or calculating the healing effect, in which a shape-based propagation may be used. For refractive cases, a Munnerlyn shape or equation can be used to construct an ideal shape. For therapeutic applications, a wavefront shape or Zernike equation can be used.

G. Real Ablation

A simulator may include a real ablation module 270. Due to the imperfection of the components in the refractive surgery system, error can be introduced in the real ablation. Most, if not all, of the components can induce high order aberrations, and some errors appear to be random. As data from the treatment table is processed by the simulator, the source errors are compiled in the real ablation module 270. This may reflect laser tissue interaction, which deals with biomechanics on the cornea. It may also include the healing effect, which can be modeled as a low-pass filter. Relatedly, as a LASIK flap is cut, a microkeratome effect can be included. Registration error as well as tracking error can be considered. The laser delivery system itself can induce further errors. Healing effects can also be considered.

H. Comparison

A simulator may include a comparison module 280. Two surfaces can be compared, on a point by point basis. The results on error can be the overall RMS error. This process can be repeated with random samples 290 to simulate the randomness of different errors.

After healing, it may be desirable to compare the final shape to the original, or ideal, shape, repeatedly several times against each modified real ablation to calculate the statistics. Simulator errors, except for fitting error and wavefront device error, can be represented in real ablation 270.

About 100 to about 1000 cases can be generated, each of which would have random walk based on time, so that the pulses in the treatment table may not exactly land on the expected location. The simulator can add up the pulses and can calculate the difference between the target shape and the model shape. Finally averages for those about 100 to about 1000 wavefronts can be calculated to obtain the RMS error.

I. Random Samples

A simulator may include a random sample module 290. Each of the random samples generated by module 290 can contain different errors. In some embodiments, module 290 can generate 100 random samples, and each is iteratively cycled through the real ablation module 270 for comparison with the ideal ablation module 260.

Modeled ablations of multiple (e.g. 100) surfaces can be used to simulate the random errors introduced by system parameters such as registration, tracking, and laser beam variability. Root-mean-squares (RMS) errors can be used as a performance metric. Multiple simulations can be run to eliminate bias.

To simulate the eye motion, a model of combined smooth pursuit and saccadic motion can be used. The model is a random walk of position (constructed with known distance and random angle) in a certain speed with certain duration. These are the parameters considered for smooth pursuit. The saccadic motion part can be constrained such that when the accumulated eye motion deviates a certain amount from a fixed target, then it quickly drifts back to origin. The model speed can be 2 mm/s and the duration can be 22 ms. The saccadic limit can be ±0.25 mm with a weight of (0.5+rand( )).

The rand( ) represents a random number generator, and generates a number having a value ranging from 0 to 1. If the eye motion goes beyond the weighted limit, one saccadic motion would move it back to zero.

FIG. 15A depicts the simulated X motion, and FIG. 15B depicts the simulated Y motion. When comparing FIGS. 14A and 14B to FIGS. 15A and 15B, the simulated motion appears similar to the real eye motion.

Simulation

| StDev | X = 0.087 mm | Y = 0.099 mm |
|---|---|---|
| Mean | X = −0.027 mm | Y = −0.029 mm |

Real Eye

| St Dev | X = 0.093 mm | Y = 0.134 mm |
|---|---|---|

J. Adjustments

The present invention also provides for simulation of system parameter adjustments. It may be desirable to adjust a set of refractive surgery system parameters based on a metric such as an accuracy variable, a heating variable, or a treatment time variable. In some embodiments, the model optical surface shape can correspond to a post-operative optical surface shape such as a healed cornea. By adjusting the set of parameters, it is possible to inhibit aberrations in the post operative optical surface shape. Simulators can assist in evaluating parameter adjustments to inhibit aberrations.

For example, to inhibit an increase in high order aberrations post-operatively, the wavefront device can have a per-term accuracy of about 0.0183 to about 0.0333 µm when a set of 6-order Zernike polynomials are used. Relatedly, the target optical surface shape can include a set of 6-order Zernike polynomials, and the set of refractive surgery system parameters can be adjusted such that each component of a post-operative total high order RMS does not exceed about 0.0061 to about 0.0111 µm. Further, the set of refractive surgery system parameters can be adjusted such that a post-operative total high order RMS is substantially equivalent to a pre-operative total high order RMS. What is more, the set of refractive surgery system parameters can be adjusted such that a post-operative total high order RMS is less than a pre operative total high order RMS. The set of refractive surgery system parameters can also be adjusted such that a post-operative total high order RMS is about one third the amount of a pre operative total high order RMS. The procedure includes error evaluation of wavefront device, registration, fitting, tracking, and laser beam uniformity and variability.

Relatedly, to correct or inhibit high order aberrations, the total RMS error can be limited to less than the pre-operative high order RMS. In general, the pre-operative eyes have an average high order RMS on the order of 0.3 µm. Assuming a 7 component system, each component having an equal limitation, this leads to a maximum limit of 0.113 µm for each component. This can keep a high order RMS from increasing post-operatively. In other embodiments, where the total RMS error is about 0.1 µm to about 0.3 µm an and the system includes 3 components, the set of refractive surgery system parameters can be adjusted such that each system component of the total high order RMS does not exceed from about 0.0111 µm to about 0.0333 µm. In yet other embodiments, where the total RMS error is about 0.1 µm to about 0.3 µm and the system includes 10 components, the set of refractive surgery system parameters can be adjusted such that each system component of the total high order RMS does not exceed from about 0.0061 µm to about 0.0111 µm.

To correct high order aberrations, however, it is possible the limitation can be a few times lower as evaluated on terms of total RMS error. For example, assuming a three-fold increase, that is, 0.1 µm total high order RMS, 0.038 µm is the limitation for each component. This can result in a reduced post-treatment error as compared to the pre-treatment error.

Similarly, to correct high order aberrations, the registration accuracy can be within 10 µm in both vertical and horizontal direction and rotational error within half a degree for VSS. For FSS, the registration accuracy should be less than 10 µm and the rotation accuracy should be less than half a degree. The healing effect can be modeled after each source of error is evaluated. This healing effect, which can be modeled as low pass filter, can effectively decrease the total RMS errors.

The principles of the present invention can be used as guidelines for developing next generation refractive systems, and can also be used as guidelines for individual eye surgeries with existing systems. These principles can also be used to develop strategies for improving parameters of existing systems. For example, by idealizing certain components, i.e. attributing no error to all components but one, it is possible to determine how much error of the total error is associated with the specific component.

In some embodiments, several components of the wavefront/laser system can be controlled to correct high order aberrations in, for example, VISX variable spot scanning (VSS) or flying spot scanning systems (FSS). In a refractive surgery system, discrete pulses can be applied to fit the surface or model optical surface shape. The total error can be associated with model surface shape, or total RMS after surgery.

Once a laser simulator is constructed, and simulation procedures are followed, design guidance can be obtained by plugging in the maximum allowable high order RMS errors for each component. Essentially, design guidance is the design of a laser ablation system involving different components. Relatedly, a simulator can be used to evaluate error source effects.

System performance evaluation for laser vision correction can include all possible error sources, such as errors from wavefront device, fitting, registration, tracking, laser delivery system, LASIK flap effect as well as healing effect. Each component can be considered separately. To evaluate the overall effect, it may be desirable to consider all components at the same time. In some embodiments, tracking, registration, wavefront device as well as LASIK flap effect are the major error sources; whereas fitting and laser beam variability are the minor sources.

It can be appreciated by one of skill in the art that all parameters, variables, factors, and the like can be incorporated into method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to lasers. Therefore, the scope of the present invention is limited solely by the appended claims.

What is claimed is:

1. A system for inhibiting an induced aberration resulting from refractive surgery, the system comprising:
   an input device that accepts a target optical surface shape;
   a determination module that determines a model optical surface shape based on the target optical surface shape and a set of refractive surgery system parameters, wherein the set of refractive surgery system parameters is embodied within a data file;
   a comparison module that compares the target optical surface shape and the model optical surface shape to determine an aberration induced by the set of refractive surgery system parameters embodied within the data file;

an adjustment module that adjusts the set of refractive surgery system parameters embodied within the data file so as to inhibit the induced aberration; and a laser that produces a laser beam directed to an eye of a patient in accordance with the adjusted set of refractive surgery system parameters.

2. The system of claim 1, wherein the set of refractive surgery system parameters comprises at least one member selected from the group consisting of a wavefront device variable, a laser ablation profile variable, a laser registration and tracking system variable, a microkeratome variable, and a healing effect variable.

3. The system of claim 2, wherein the wavefront device variable comprises a member selected from a group consisting of a spot identification factor, an accommodation factor, and a reconstruction factor.

4. The system of claim 3, wherein the reconstruction factor comprises a member selected from the group consisting of uncompensated residual error portion, a measurement error portion, and a remaining error portion.

5. The system of claim 2, wherein the laser ablation profile variable comprises a member selected from the group consisting of a pulse size factor, a spot size variability factor, a beam uniformity factor, and an ablation rate factor.

6. The system of claim 2, wherein the microkeratome variable comprises a member selected from the group consisting of a central flattening and peripheral thickening effect factor and a hinge effect factor.

7. The system of claim 2, wherein the laser registration and tracking system variable comprises a member selected from the group consisting of a registration factor, a linear tracking factor, and a torsional tracking factor.

8. The system of claim 2, wherein the wavefront device variable is configured to address a high order aberration.

9. The system of claim 6, wherein the flying spot scanning factor is about 1.5 mm.

10. The system of claim 2, wherein the wavefront device variable comprises a gridsize factor adjusted to about 100 µm, and the laser ablation profile variable comprises a flying spot scanning factor adjusted to range from about 1 mm to about 1.6 mm.

11. The system of claim 2, wherein the wavefront device variable comprises a spot identification error adjusted to about 0.05 microns; or wherein the wavefront device variable comprises a wavefront reconstruction error adjusted to about 0.05 microns; or wherein the wavefront device variable comprises an accommodation error adjusted to about 0.25D, equivalent to 0.325 microns RMS error for a 6 mm pupil.

12. The system of claim 2, wherein the microkeratome variable comprises an induced positive spherical aberration adjusted to between about 0.1 microns and about 0.3 microns; or wherein the microkeratome variable comprises a coma in the direction of the microkeratome hinge adjusted to an amount between 0.1 microns and 0.3 microns.

13. The system of claim 2, wherein the healing effect variable comprises a Gaussian kernel adjusted to about 2 micron in height and about 0.5 mm in full width at half maximum (FWHM).

14. The system of claim 2, wherein the laser ablation profile variable comprises a variable spot scanning factor, and the laser registration and tracking system variable comprises a registration accuracy adjusted to less than 10 µm in both the vertical and horizontal directions and a rotational error adjusted to less than 0.5°; or wherein the laser ablation profile variable comprises a flying spot scanning factor, and the laser registration and tracking system variable comprises a registration accuracy adjusted to less than 10 µm in both the vertical and horizontal directions and a rotational error adjusted to less than 0.5°; or wherein the laser ablation profile variable comprises a variable spot scanning factor, and the laser registration and tracking system variable comprises a tracking accuracy adjusted to less than 20 µm in both the vertical and horizontal directions, a latency time adjusted to less than 10 ms, and a tracking speed adjusted to 60 Hz or greater; or wherein the laser ablation profile variable comprises a flying spot scanning factor, and the laser registration and tracking system variable comprises a tracking accuracy adjusted to less than 5 µm in both the vertical and horizontal directions, a latency time adjusted to less than 5 ms, and a tracking speed adjusted to 200 Hz or greater; or wherein the laser ablation profile variable comprises a variable spot scanning factor, and the laser registration and tracking system variable comprises a cyclo-torsional tracking angular accuracy adjusted to 0.5° or better; or wherein the laser ablation profile variable comprises a flying spot scanning factor, and the laser registration and tracking system variable comprises a cyclo-torsional tracking angular accuracy adjusted to 0.25° or better; or wherein the laser ablation profile variable comprises a variable spot scanning factor, and the laser registration and tracking system variable comprises a laser energy fluctuation adjusted to less than 4%; or wherein the laser ablation profile variable comprises a flying spot scanning factor, and the laser registration and tracking system variable comprises a laser energy fluctuation adjusted to less than 2%.

15. The system of claim 2, wherein the target optical surface shape comprises a set of 6-order Zernike polynomials, and the set of refractive surgery system parameters is adjusted such that each component of a post-operative total high order RMS does not exceed about 0.025 µm; or wherein the target optical surface shape comprises a set of 6-order Zernike polynomials, and the set of refractive surgery system parameters is adjusted such that each component of a post-operative total high order RMS does not exceed about 0.0087 µm.

16. The system of claim 1, wherein the adjustment module comprises a metric selected from the group consisting of an accuracy variable, a heating variable, and a treatment time variable.

17. The system of claim 16, wherein the accuracy variable is based on a root mean squares error factor, or wherein the heating variable is based on a temperature factor, or wherein the treatment time variable is based on an ablation time factor.

18. The system of claim 1, wherein the aberration comprises a high order aberration.

19. The system of claim 1, wherein the target optical surface shape is configured to address a low order aberration.

20. The system of claim 1, wherein the adjustment module is configured to adjust the set of refractive surgery system parameters such that a post-operative total high order RMS of about 0.3 µm is achieved.

21. The system of claim 20, wherein a pre-operative total high order RMS is about 0.3 µm.

22. The system of claim 20, wherein each component of the total high order RMS does not exceed about 0.13 µm.

23. The system of claim 1, wherein the adjustment module is configured to adjust the set of refractive surgery system parameters such that a post-operative total high order RMS of about 0.1 µm is achieved.

24. The system of claim 23, wherein a pre-operative total high order RMS is about 0.3 µm.

25. The system of claim 23, wherein each component of the total high order RMS does not exceed about 0.045 µm.

26. The system of claim 1, wherein the adjustment module is configured to adjust the set of refractive surgery system parameters such that a post-operative total high order RMS is substantially equivalent to a pre-operative total high order RMS; or
   wherein the adjustment module is configured to adjust the set of refractive surgery system parameters such that a post-operative total high order RMS is less than a pre-operative total high order RMS; or
   wherein the adjustment module is configured to adjust the set of refractive surgery system parameters such that a post-operative total high order RMS is about one third the amount of a pre-operative total high order RMS.

27. A system for altering aberration distribution resulting from optical surface refractive surgery, the system comprising:
   an input device that accepts a target optical surface shape;
   a determination module that determines a model optical surface shape based on the target optical surface shape and a set of refractive surgery system parameters, wherein the set of refractive surgery system parameters is embodied within machine readable data of a tangible storage media;
   a comparison module that compares the target optical surface shape and the model optical surface shape to determine an aberration distribution;
   an adjustment module that adjusts the set of refractive surgery system parameters embodied within machine readable data of the tangible storage media so as to alter the aberration distribution; and
   a laser that produces a laser beam directed to an eye of a patient in accordance with the adjusted set of refractive surgery system parameters.

28. A system for inhibiting a refractive surgery induced aberration, the system comprising:
   an input device that accepts a target optical surface shape;
   a determination module that determines a model optical surface shape based on the target optical surface shape and a set of refractive surgery system parameters, the model optical surface shape having an aberration, wherein the set of refractive surgery system parameters is embodied within a storage module;
   an adjustment module that adjusts the set of refractive surgery system parameters embodied within the storage module so as to inhibit the aberration; and
   a laser that produces a laser beam directed to an eye of a patient in accordance with the adjusted set of refractive surgery system parameters.

* * * * *